(12) United States Patent
Vanoppen et al.

(10) Patent No.: US 9,964,853 B2
(45) Date of Patent: May 8, 2018

(54) METHOD OF DETERMINING DOSE AND FOCUS, INSPECTION APPARATUS, PATTERNING DEVICE, SUBSTRATE AND DEVICE MANUFACTURING METHOD

(71) Applicant: ASML Netherlands B.V., Veldhoven (NL)

(72) Inventors: Peter Clement Paul Vanoppen, Hechtel-Eksel (BE); Eric Jos Anton Brouwer, Den Bosch (NL); Hugo Augustinus Joseph Cramer, Eindhoven (NL); Jan Hendrik Den Besten, Eindhoven (NL); Adrianus Franciscus Petrus Engelen, Waalre (NL); Paul Christiaan Hinnen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days. days.

(21) Appl. No.: 14/648,445

(22) PCT Filed: Nov. 22, 2013

(86) PCT No.: PCT/EP2013/074516
§ 371 (c)(1),
(2) Date: May 29, 2015

(87) PCT Pub. No.: WO2014/082938
PCT Pub. Date: Jun. 5, 2014

(65) Prior Publication Data
US 2015/0293458 A1  Oct. 15, 2015

Related U.S. Application Data

(60) Provisional application No. 61/731,947, filed on Nov. 30, 2012, provisional application No. 61/746,384, filed on Dec. 27, 2012.

(51) Int. Cl.
*G03B 27/52* (2006.01)
*G03F 7/20* (2006.01)
*G01N 21/47* (2006.01)

(52) U.S. Cl.
CPC ..... *G03F 7/70058* (2013.01); *G01N 21/4738* (2013.01); *G03F 7/70558* (2013.01);
(Continued)

(58) Field of Classification Search
CPC ............ G03F 7/70558; G03F 7/70058; G03F 7/70625; G03F 7/70641; G03F 7/70683
See application file for complete search history.

(56) References Cited

U.S. PATENT DOCUMENTS 5,674,650 A   10/1997 Dirksen et al.
6,251,544 B1  6/2001 Inoue et al.
(Continued)

FOREIGN PATENT DOCUMENTS

CN  102422227 A  4/2012
EP  1 881 374 A2  1/2008
(Continued)

OTHER PUBLICATIONS

International Search Report directed to related International Patent Application No. PCT/EP2013/074516, mailed Mar. 25, 2014; 4 pages.
(Continued)

*Primary Examiner* — Deoram Persaud
(74) *Attorney, Agent, or Firm* — Sterne, Kessler, Goldstein & Fox P.L.L.C.

(57) ABSTRACT

A method of determining exposure dose of a lithographic apparatus used in a lithographic process on a substrate. Using the lithographic process to produce a first structure on the substrate, the first structure having a dose-sensitive feature which has a form that depends on exposure dose of
(Continued)

the lithographic apparatus on the substrate. Using the lithographic process to produce a second structure on the substrate, the second structure having a dose-sensitive feature which has a form that depends on the exposure dose of the lithographic apparatus but which has a different sensitivity to the exposure dose than the first structure. Detecting scattered radiation while illuminating the first and second structures with radiation to obtain first and second scatterometer signals. Using the first and second scatterometer signals to determine an exposure dose value used to produce at least one of the first and second structures.

27 Claims, 17 Drawing Sheets

(52) U.S. Cl.
CPC ...... *G03F 7/70625* (2013.01); *G03F 7/70641* (2013.01); *G03F 7/70683* (2013.01)

(56) References Cited

U.S. PATENT DOCUMENTS

| | | | |
|---|---|---|---|
| 6,879,400 B2 | 4/2005 | Ausschnitt et al. | |
| 7,352,453 B2 | 4/2008 | Mieher et al. | |
| 7,439,001 B2* | 10/2008 | Ausschnitt | G03F 7/70533 430/30 |
| 7,667,842 B2 | 2/2010 | Schulz | |
| 7,700,247 B2 | 4/2010 | Ausschnitt | |
| 7,771,905 B2* | 8/2010 | Sentoku | G03F 7/70641 430/22 |
| 7,916,284 B2 | 3/2011 | Dusa et al. | |
| 8,830,447 B2 | 9/2014 | Den Boef et al. | |
| 8,994,944 B2* | 3/2015 | Cramer | G03F 7/70641 356/399 |
| 2004/0058256 A1* | 3/2004 | Fujisawa | G03F 7/70558 430/30 |
| 2004/0190008 A1 | 9/2004 | Mieher et al. | |
| 2004/0233445 A1* | 11/2004 | Littau | G01N 21/4788 356/401 |
| 2005/0018164 A1 | 1/2005 | Hansen | |
| 2005/0173634 A1 | 8/2005 | Wong et al. | |
| 2006/0146310 A1* | 7/2006 | De Kruif | G03F 7/70558 355/69 |
| 2006/0170899 A1* | 8/2006 | De Kruif | G03F 7/70625 355/69 |
| 2007/0050749 A1* | 3/2007 | Ye | G03F 1/44 430/30 |
| 2008/0018874 A1* | 1/2008 | Dusa | G03F 7/70516 355/55 |
| 2010/0075238 A1* | 3/2010 | Fonseca | G03B 27/54 430/30 |
| 2010/0201963 A1 | 8/2010 | Cramer et al. | |
| 2010/0221659 A1 | 9/2010 | Ebata et al. | |
| 2010/0328636 A1* | 12/2010 | Quaedackers | G03F 7/70625 355/53 |
| 2011/0027704 A1 | 2/2011 | Cramer et al. | |
| 2011/0043791 A1 | 2/2011 | Smilde et al. | |
| 2011/0109888 A1 | 5/2011 | Van Der Schaar et al. | |
| 2011/0249247 A1* | 10/2011 | Cramer | G03F 1/14 355/55 |
| 2011/0295555 A1 | 12/2011 | Meessen et al. | |
| 2012/0044472 A1* | 2/2012 | Den Boef | G03F 7/70641 355/55 |
| 2012/0123581 A1* | 5/2012 | Smilde | G03F 7/70483 700/105 |
| 2012/0206703 A1* | 8/2012 | Bhattacharyya | G03F 7/70633 355/67 |
| 2013/0217154 A1 | 8/2013 | Fukazawa et al. | |
| 2014/0307256 A1 | 10/2014 | Amir | |
| 2015/0293458 A1 | 10/2015 | Vanoppen et al. | |
| 2015/0308966 A1* | 10/2015 | Grootjans | G01N 21/95607 355/67 |
| 2015/0338749 A1 | 11/2015 | Hinnen et al. | |
| 2016/0026096 A1* | 1/2016 | Verma | G01N 21/4738 355/67 |
| 2016/0061589 A1* | 3/2016 | Bhattacharyya | G01B 11/14 356/620 |
| 2016/0061750 A1* | 3/2016 | Den Boef | G01B 11/00 355/67 |
| 2016/0116849 A1* | 4/2016 | Cramer | G03F 7/70133 355/67 |
| 2016/0146740 A1* | 5/2016 | Lu | G01B 11/272 356/620 |
| 2016/0180517 A1* | 6/2016 | Fuchs | G06T 7/11 382/144 |
| 2016/0274456 A1* | 9/2016 | Chen | G03F 7/70625 |
| 2016/0313654 A1* | 10/2016 | Zeng | G03F 7/70633 |
| 2016/0363871 A1* | 12/2016 | Van Oosten | G03F 7/70516 |
| 2016/0370710 A1* | 12/2016 | Wardenier | G01B 11/03 |
| 2017/0059999 A1* | 3/2017 | Van Der Schaar | G01N 21/47 |
| 2017/0090302 A1* | 3/2017 | Slotboom | G03F 7/70625 |

FOREIGN PATENT DOCUMENTS

| | | |
|---|---|---|
| JP | H09-504142 | 4/1997 |
| JP | 2010-133941 A | 6/2010 |
| TW | 1537688 B | 6/2016 |
| WO | WO 99/45340 A1 | 9/1999 |
| WO | WO 2009/051088 A1 | 4/2009 |
| WO | WO 2009/078708 A1 | 6/2009 |
| WO | WO 2009/106279 A1 | 9/2009 |
| WO | WO 2010/012624 A1 | 2/2010 |
| WO | WO 2013/189724 A2 | 12/2013 |
| WO | WO 2012/056601 | 3/2014 |
| WO | WO 2014/082938 A1 | 6/2014 |
| WO | WO 2015/153497 A1 | 10/2017 |

OTHER PUBLICATIONS

International Preliminary Report on Patentability and Written Opinion of the International Searching Authority directed to related International Patent Application No. PCT/EP2013/074516, issued Jun. 2, 2015; 8 pages.

U.S. Appl. No. 14/410,496, Hinnen et al., "Method of Determining Focus, Inspection Apparatus, Patterning Device, Substrate and Device Manufacturing Method," filed Dec. 22, 2014.

International Preliminary Report on Patentability and Written Opinion of the International Searching Authority directed to related International Patent Application No. PCT/EP2015/062778, dated Jan. 3, 2017; 8 pages.

International Search Report directed to related International Patent Application No. PCT/EP2015/062778, dated Oct. 19, 2015; 3 pages.

Japanese Search Report by Registered Searching Organization from related Japanese Patent Publication No. JP 2017521709 A, dated Jan. 24, 2018; 30 pages.

\* cited by examiner (a)

(b)  (c)  (d)

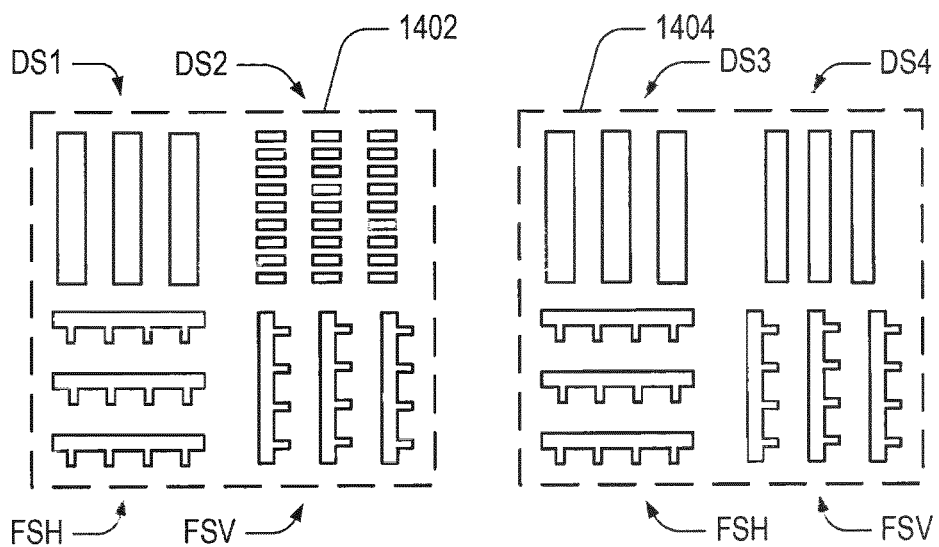
Fig. 14a                    Fig. 14b
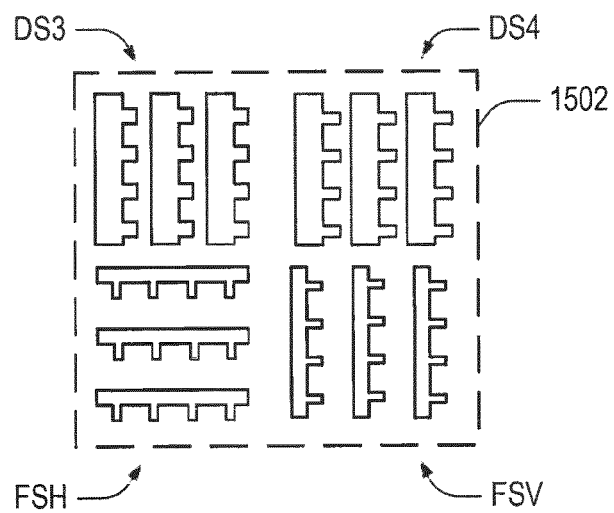
Fig. 15

METHOD OF DETERMINING DOSE AND FOCUS, INSPECTION APPARATUS, PATTERNING DEVICE, SUBSTRATE AND DEVICE MANUFACTURING METHOD

CROSS REFERENCE TO RELATED APPLICATIONS

This application is related to U.S. Provisional Patent Application No. 61/731,947, filed Nov. 30, 2012 and U.S. Provisional Application No. 61/746,384 filed Dec. 27, 2012 which are incorporated by reference herein in its entirety.

BACKGROUND

Field of the Invention

The present invention relates to methods and apparatus for determining exposure dose and focus of a lithographic apparatus usable, for example, with pupil-plane detection or dark-field scatterometry in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment of two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark-field scatterometry in which the zeroth order of diffraction (corresponding to a specular reflection) is blocked, and only higher orders processed.

Diffraction-based overlay using dark-field detection of the diffraction orders enables overlay measurements on smaller targets. These targets can be smaller than the illumination spot and may be surrounded by product structures on a wafer. Multiple targets can be measured in one image.

In the known metrology technique, overlay measurement results are obtained by measuring the target twice under certain conditions, while either rotating the target or changing the illumination mode or imaging mode to obtain separately the $-1^{st}$ and the $+1^{st}$ diffraction order intensities. Comparing these intensities for a given grating provides a measurement of asymmetry in the grating.

Asymmetry in a pair of stacked gratings can be used as an indicator of overlay error. Similarly, asymmetry in a focus-sensitive grating can be used as an indicator of defocus.

However, any effect that leads to an asymmetry change in the scatterometer pupil will be attributed to scanner defocus. One such effect is that of exposure dose. Exposure dose variation is difficult to measure, especially with small in-die targets.

The effective exposure dose, arising from the combination of lithographic apparatus, reticle and processing, is typically measured through line width (critical dimension, CD) of critical product structures. Inspection apparatus used for such measurements includes metrology tools such as CD-SEM (Scanning Electron Microscope) and scatterometers.

However, CD-SEM is relatively slow and has noise levels of typically 0.25 nm-1 nm 3-sigma. Furthermore, although scatterometers are very sensitive metrology tools, the sensitivity is to a wide range of feature parameters. Careful scatterometer setup recipe creation and optimization is needed to separate CD variations from variations in the underlying stack of materials making up the target. Moreover, scatterometry for CD measurement typically requires large targets (for example 40×40 µm).

SUMMARY

It is desirable to measure exposure dose more directly and to improve the accuracy of the focus measurement. Furthermore, it is desired that this could be applied to small target structures that can be read out with the dark-field image-based technique.

According to a first example, there is provided a method of determining exposure dose of a lithographic apparatus used in a lithographic process on a substrate, the method comprising the steps: (a) receiving a substrate comprising first and second structure produced using the lithographic process; (b) detecting scattered radiation while illuminating the first structure with radiation to obtain a first scatterometer signal; (c) detecting scattered radiation while illuminating the second structure with radiation to obtain a second scatterometer signal; and (d) using the first and second scatterometer signals to determine an exposure dose value used to produce the first structure, based on: the first structure having at least one feature which has a form that depends on exposure dose of the lithographic apparatus on the substrate; and the second structure having at least one feature which has a form that depends on the exposure dose of the lithographic apparatus on the substrate but which has a different sensitivity to the exposure dose of the lithographic apparatus on the substrate than the first structure.

According to another example, there is provided a method of determining exposure dose of a lithographic apparatus used in a lithographic process on a substrate, the method comprising the steps: receiving a substrate comprising a third structure produced using the lithographic process; detecting scattered radiation while illuminating the third structure with radiation to obtain a third scatterometer signal; and using the third scatterometer signal to correct the exposure dose value obtained using the method of the first example for focus of the lithographic apparatus on the substrate, based on the third structure having at least one feature which has a profile that has a form that depends on focus of the lithographic apparatus on the substrate.

According to a further example, there is provided a method of determining focus of a lithographic apparatus used in a lithographic process on a substrate, the method comprising the steps: receiving a substrate comprising a third structure produced; detecting scattered radiation while illuminating the third structure with radiation to obtain a third scatterometer signal; and using the exposure dose value obtained using the method of the first example and the third scatterometer signal to determine a focus value used to produce the third structure, based on the third structure having at least one feature which has a profile that has a form that depends on focus of the lithographic apparatus on the substrate.

According to a still further example, there is provided an inspection apparatus for determining exposure dose of a lithographic apparatus used in a lithographic process on a substrate, the inspection apparatus comprising: an illumination system configured to illuminate with radiation first and second structures produced using the lithographic process on the substrate; a detection system configured to detect scattered radiation arising from illumination of the first structure to obtain a first scatterometer signal and configured to detect scattered radiation arising from illumination of the second structure to obtain a second scatterometer signal; and a processor configured to use the first and second scatterometer signals to determine an exposure dose value used to produce the first structure, based on: the first structure having at least one feature which has a form that depends on exposure dose of the lithographic apparatus on the substrate; and the second structure having at least one feature which has a form that depends on the exposure dose of the lithographic apparatus on the substrate but which has a different sensitivity to the exposure dose of the lithographic apparatus on the substrate than the first structure.

According to another example, there is provided a patterning device for determining exposure dose of a lithographic apparatus used in a lithographic process on a substrate, the patterning device comprising a target pattern comprising: a first sub-pattern configured to produce a first structure using the lithographic process, the first structure having at least one feature which has a form that depends on exposure dose of the lithographic apparatus on the substrate; and a second sub-pattern configured to produce a second structure using the lithographic process, the second structure having at least one feature which has a form that depends on the exposure dose of the lithographic apparatus on the substrate but which has a different sensitivity to the exposure dose of the lithographic apparatus on the substrate than the first structure.

According to a yet further example, there is provided a substrate for determining exposure dose of a lithographic apparatus used in a lithographic process on the substrate, the substrate comprising a target comprising: a first structure having at least one feature which has a profile that has an asymmetry that depends on the focus and the exposure dose of the lithographic apparatus on the substrate; and a second structure having at least one feature which has a profile that has a form that depends on the focus and the exposure dose of the lithographic apparatus on the substrate but which is less sensitive to the focus of the lithographic apparatus on the substrate than the first structure and which is more sensitive to the exposure dose of the lithographic apparatus than the first structure.

According to another example, there is provided a method of manufacturing devices wherein a device pattern is applied to a series of substrates using a lithographic process, the method including determining exposure dose of the lithographic apparatus using at least one of the substrates using a method according to the first example, and controlling the lithographic process for later substrates in accordance with the result of the method of determining exposure dose.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 3A-3D show (a) a schematic diagram of a dark field scatterometer for use in measuring targets according to embodiments of the invention using a first pair of illumination apertures, (b) a detail of diffraction spectrum of a target grating for a given direction of illumination (c) a second pair of illumination apertures providing further illumination modes in using the scatterometer for diffraction based overlay measurements and (d) a third pair of illumination apertures combining the first and second pair of apertures.

Figure 4:
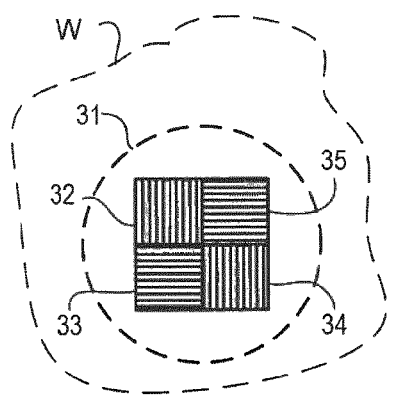

FIG. 4 depicts a known form of multiple grating target and an outline of a measurement spot on a substrate.

Figure 3:
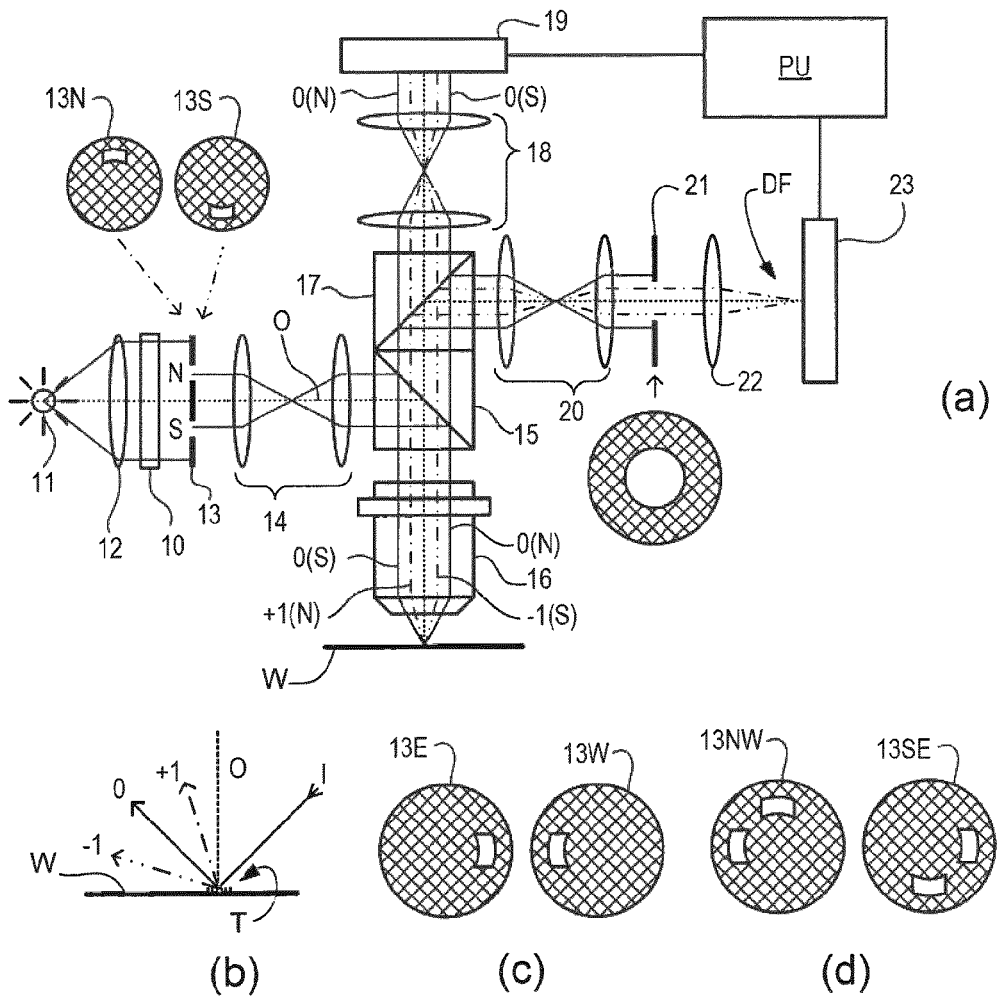
Figure 5:
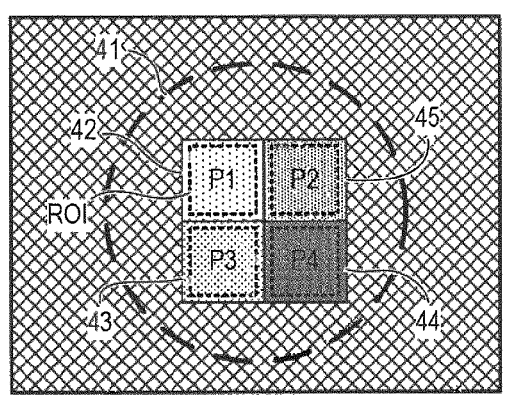

FIG. 5 depicts an image of the target of FIG. 4 obtained in the scatterometer of FIG. 3.

Figure 6:
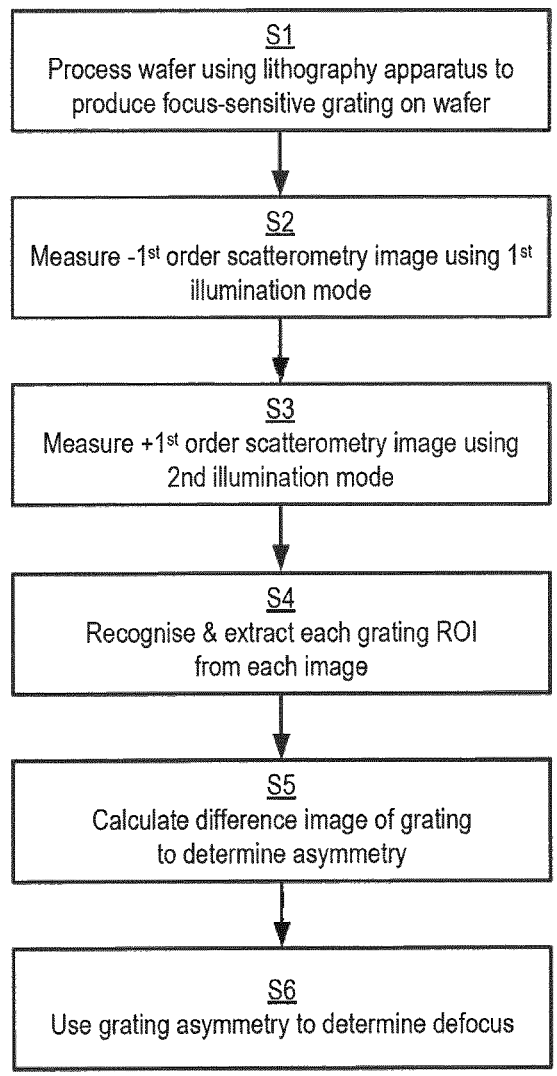

FIG. 6 is a flowchart showing the steps of a defocus measurement method using the scatterometer of FIG. 3 and adaptable to form an embodiment of the present invention.

Figure 7:
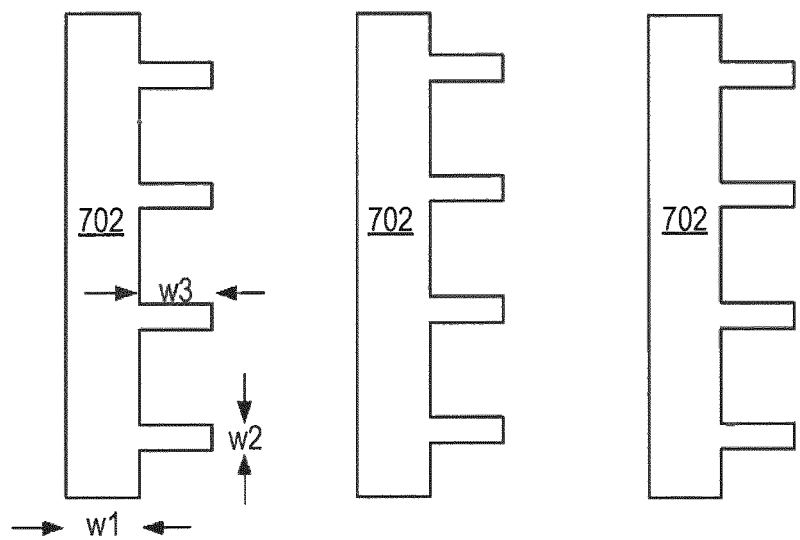

FIG. 7 illustrates a focus-sensitive asymmetric grating pattern.

Figure 8:
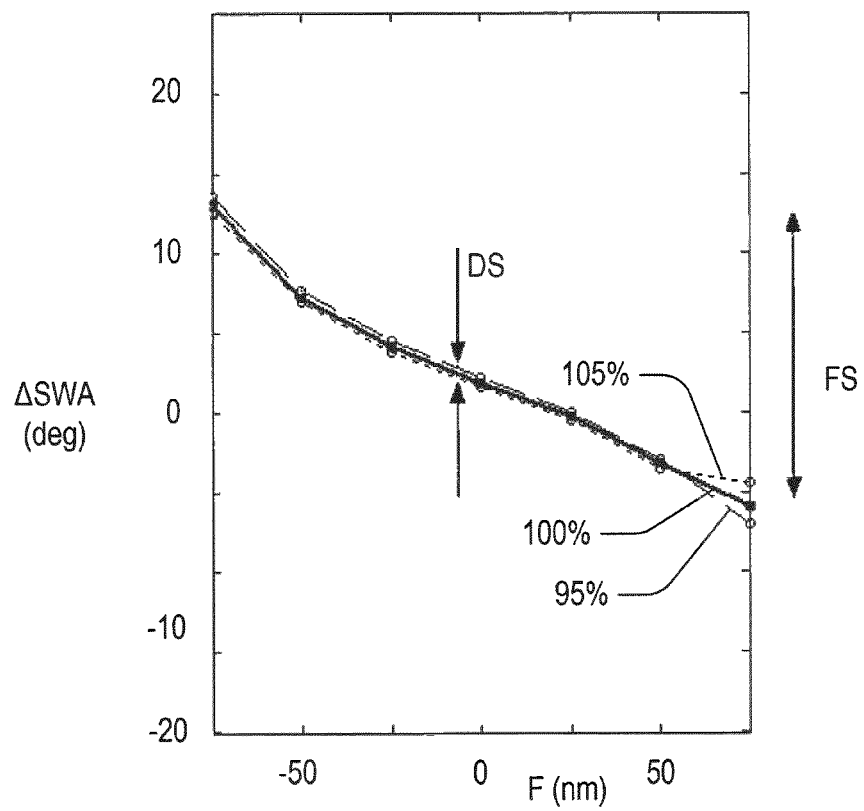

FIG. 8 is a graph that illustrates the dependence of side wall angle difference on focus setting for exposure of the grating pattern of FIG. 7.

Figure 9:
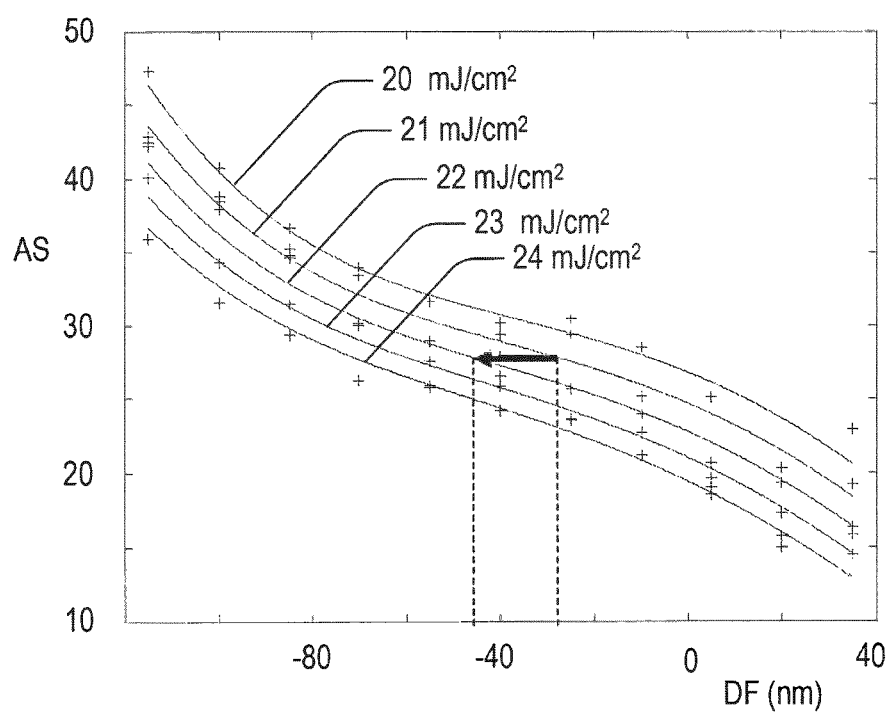

FIG. 9 is a graph of asymmetry, measured with a scatterometer, versus defocus of the lithography apparatus for exposure of a grating pattern similar to that of FIG. 7.

Figure 10A:
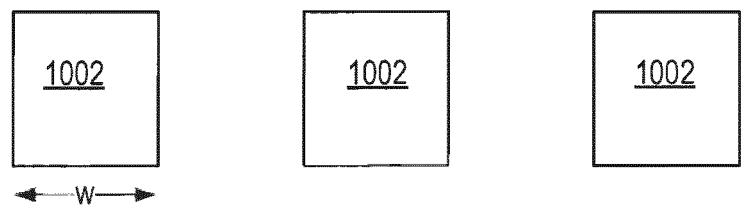
Figure 10B:
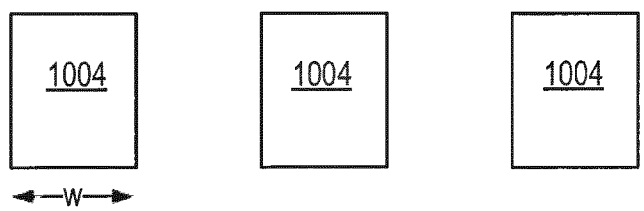

FIGS. 10a and 10b illustrate dose-sensitive symmetric grating patterns with different dose sensitivities.

Figure 11:
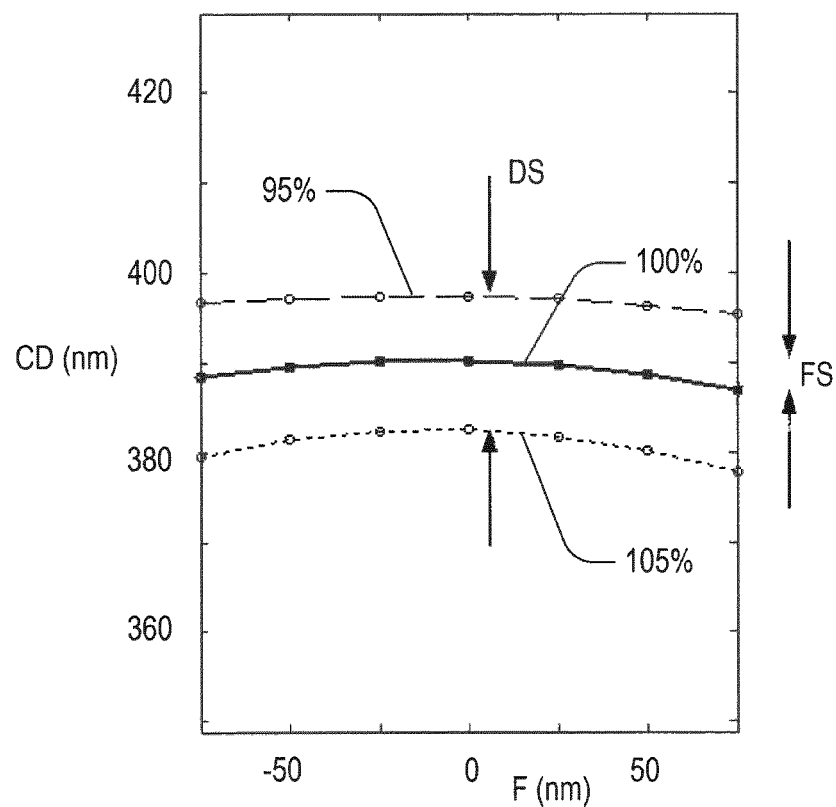

FIG. 11 is a graph that illustrates the dependence of critical dimension on focus and dose settings of the lithography apparatus for exposure of the grating pattern of FIG. 10a.

Figure 12:
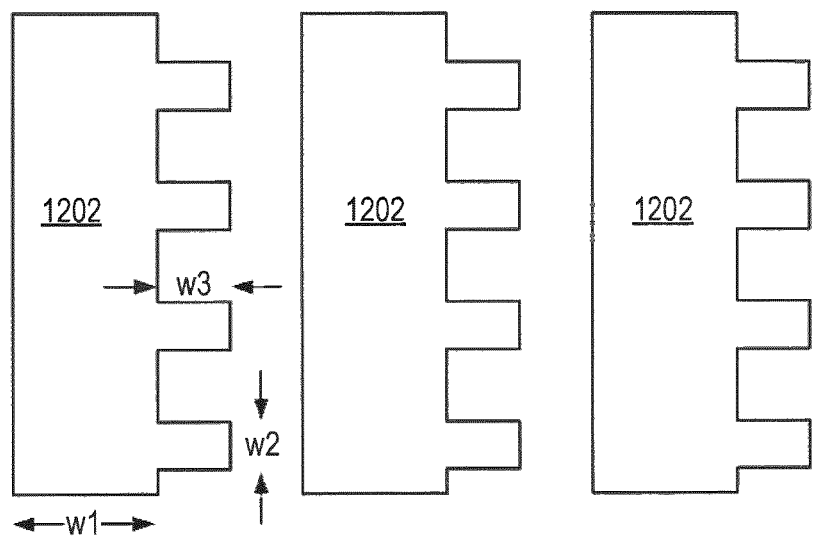

FIG. 12 illustrates a dose-sensitive asymmetric grating pattern.

Figure 13:
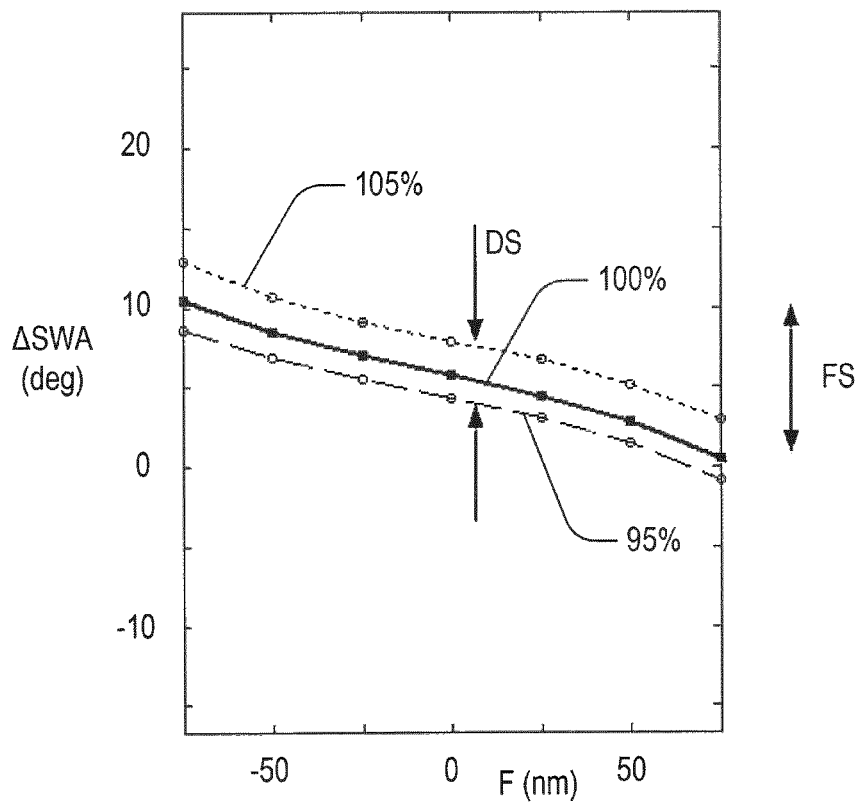

FIG. 13 is a graph that illustrates the dependence of side wall angle difference on focus and dose settings of the lithography apparatus for exposure of the grating pattern of FIG. 12.

FIGS. 14a, 14b and 15 schematically illustrate combined focus- and differential dose-sensitive targets, suitable for dark-field image-detection scatterometry.

Figure 16:
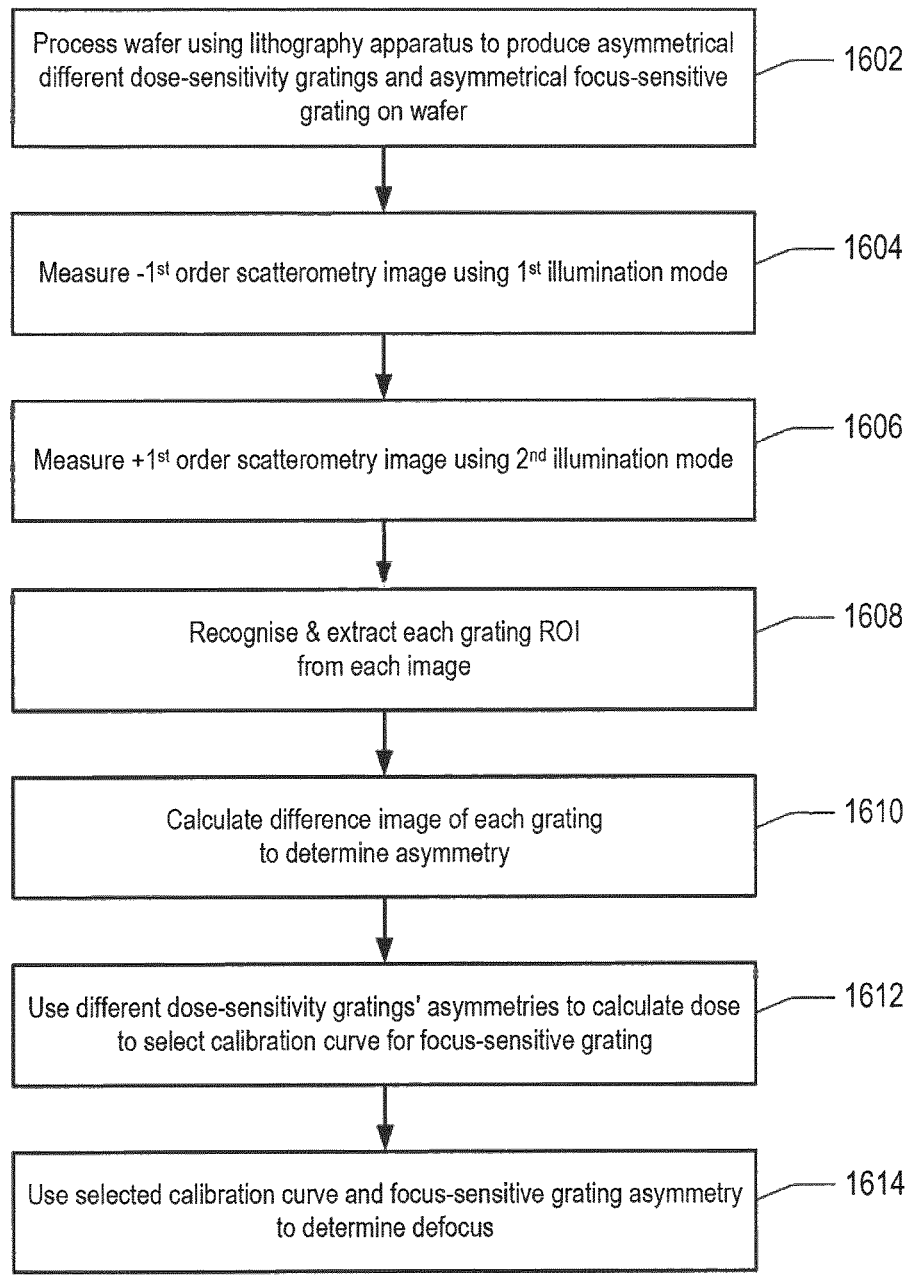

FIG. 16 is a flow chart of a method of determining dose and focus in accordance with an embodiment of the present invention using asymmetrical differential dose-sensitive gratings with dark-field scatterometry.

Figure 17:
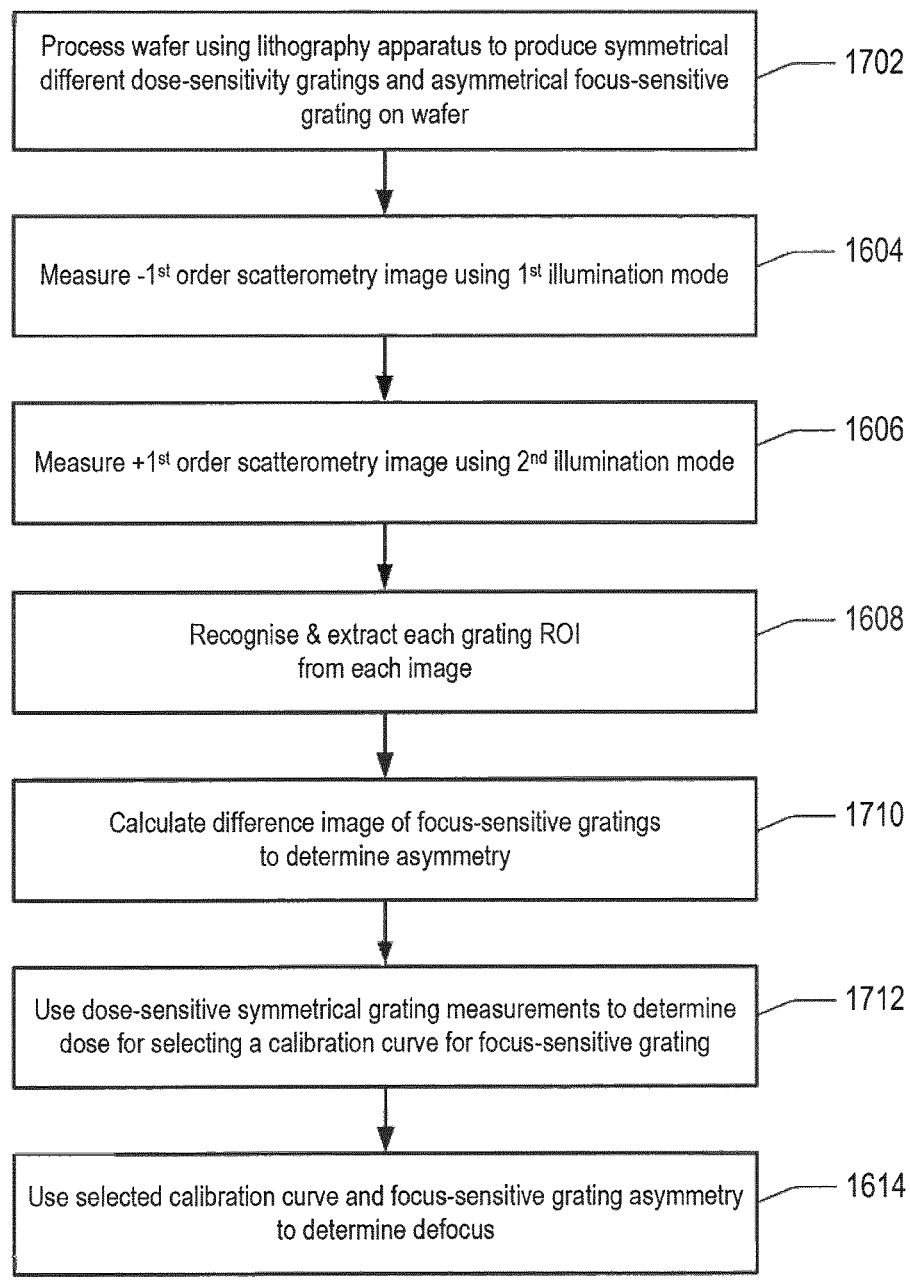

FIG. 17 is a flow chart of a method of determining dose and focus in accordance with another embodiment of the present invention using symmetrical differential dose-sensitive gratings with dark-field scatterometry.

Figure 18:
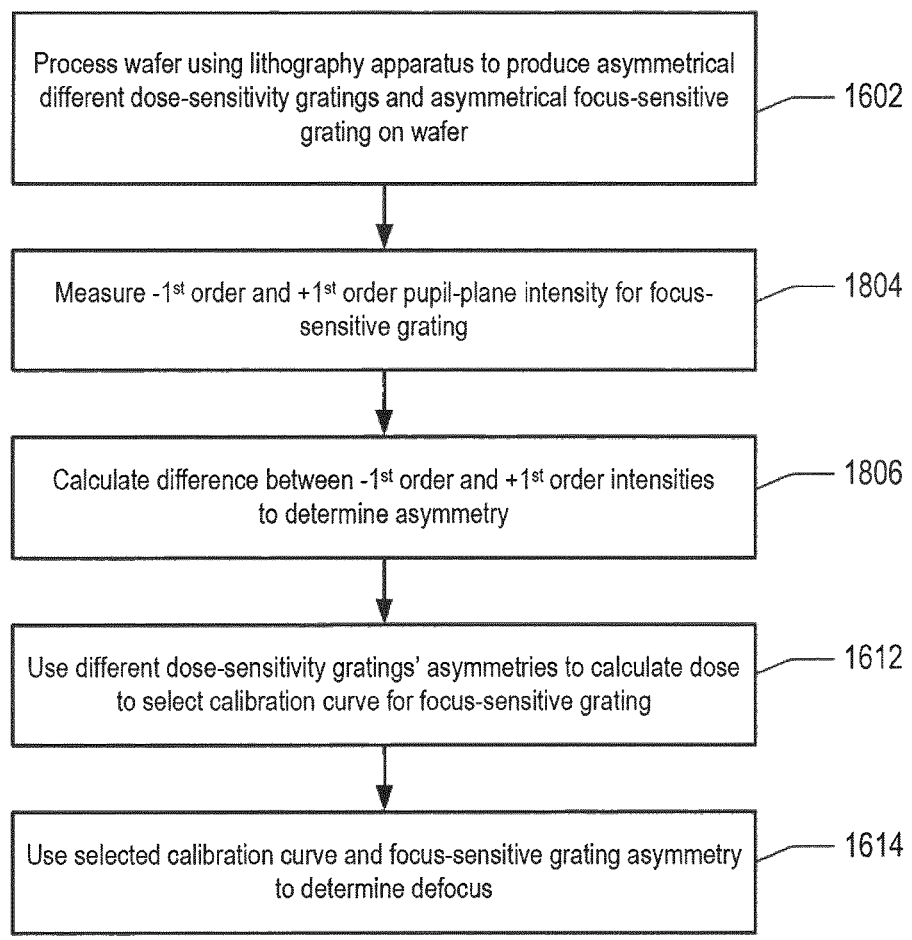

FIG. 18 is a flow chart of a method of determining dose and focus in accordance with embodiment of the present invention using asymmetrical differential dose-sensitive gratings with pupil-plane detection scatterometry.

Figure 19:
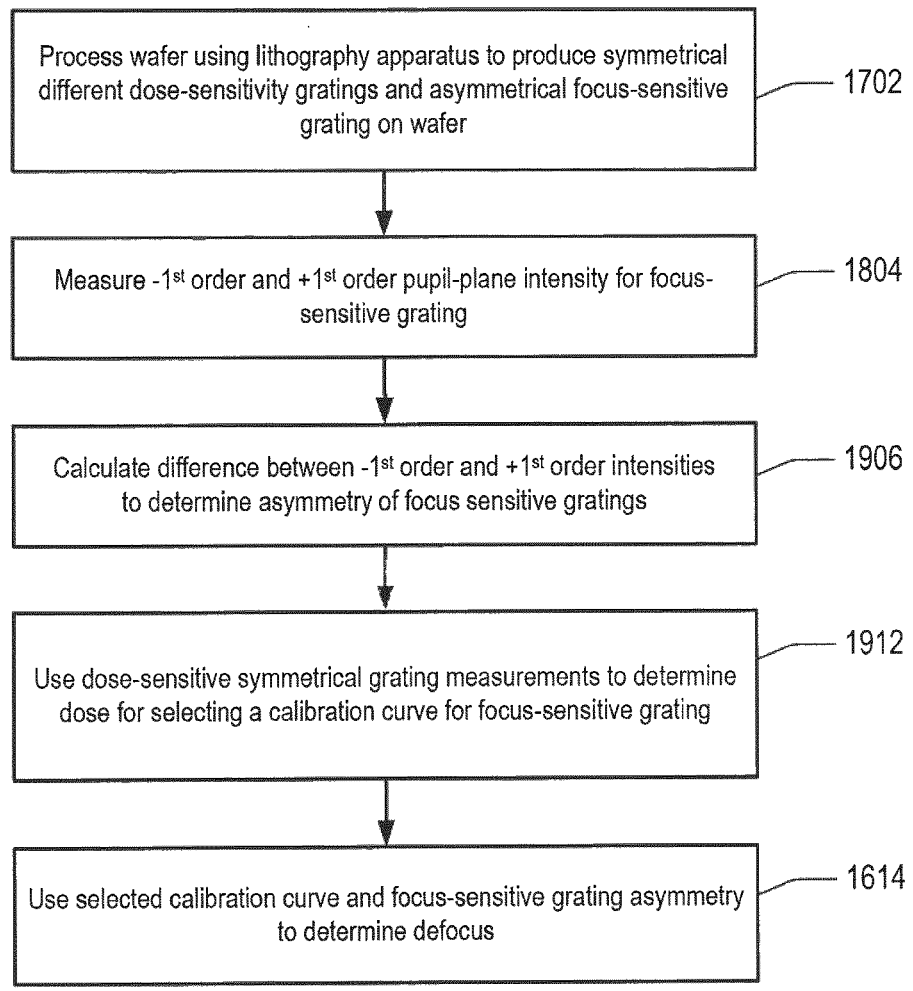

FIG. 19 is a flow chart of a method of determining dose and focus in accordance with another embodiment of the present invention using symmetrical differential dose-sensitive gratings with pupil-plane detection scatterometry.

Figure 20A:
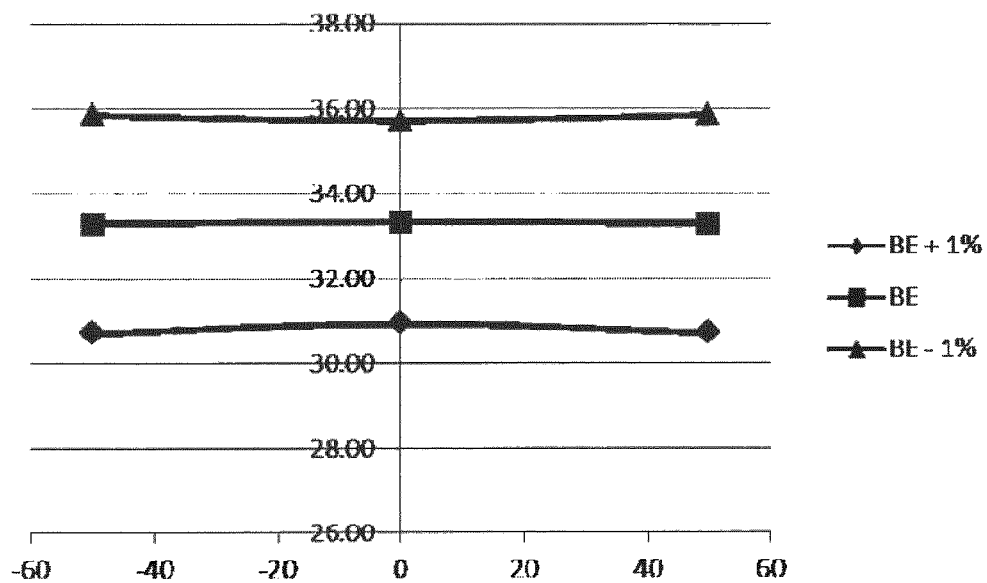
Figure 20B:
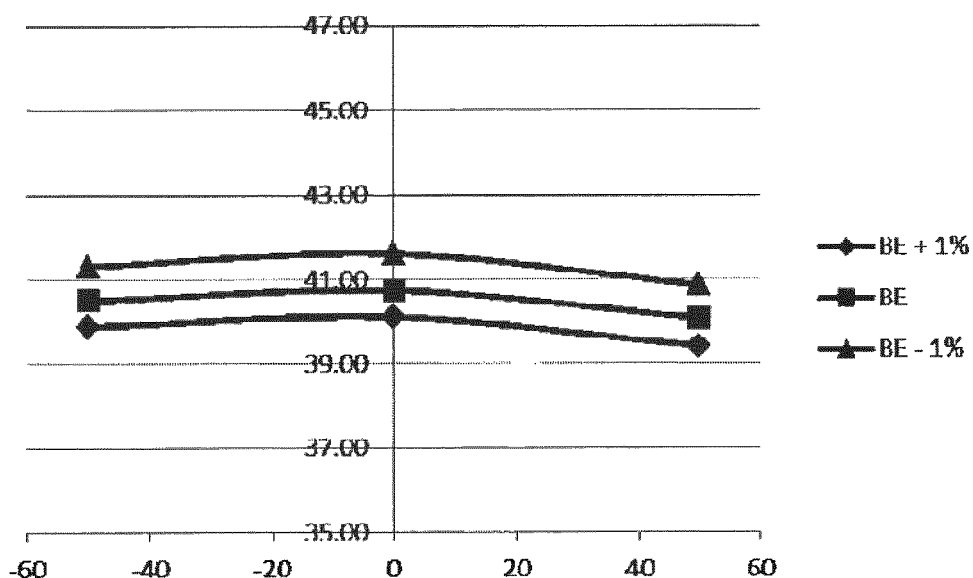

FIGS. 20a and 20b are graphs of focus versus CD (Bossung plots) for three different doses for a differential dose-sensitive pair of gratings with 80 nm and 100 nm pitch respectively.

Figure 21:
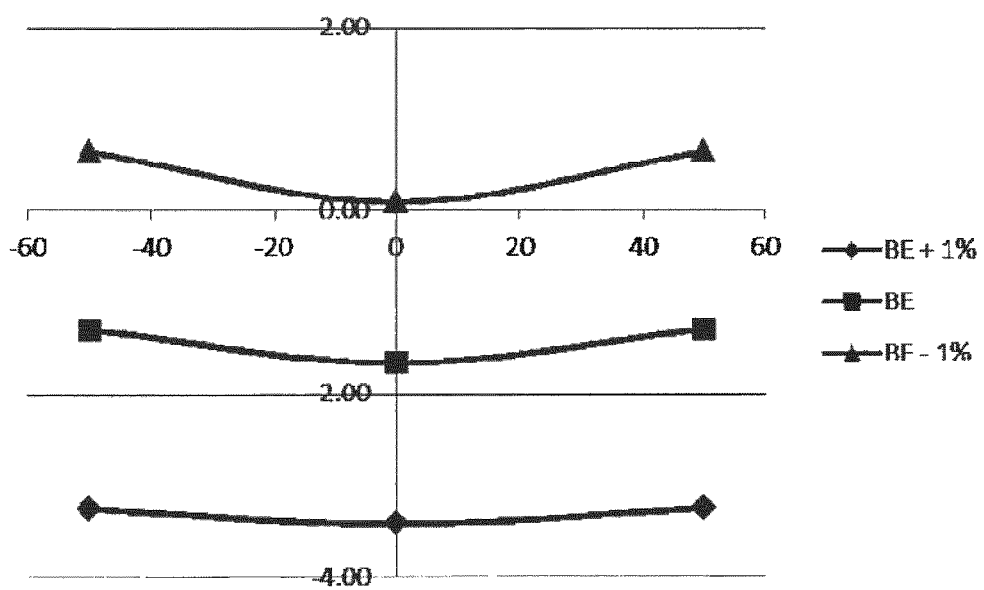

FIG. 21 is a graph of focus versus effective CD difference for three different doses, derived from the data used for FIGS. 20a and 20b.

Figure 22:
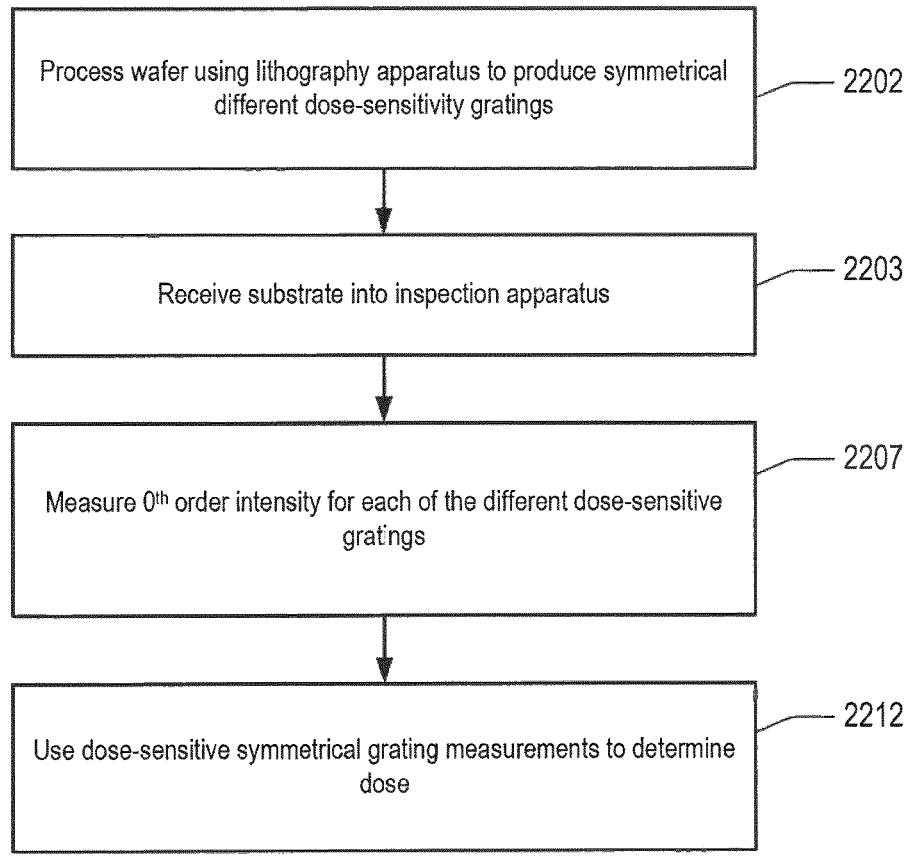

FIG. 22 is a flow chart of a method of determining dose in accordance with an embodiment of the present invention using symmetrical differential dose-sensitive gratings.

Figure 23:
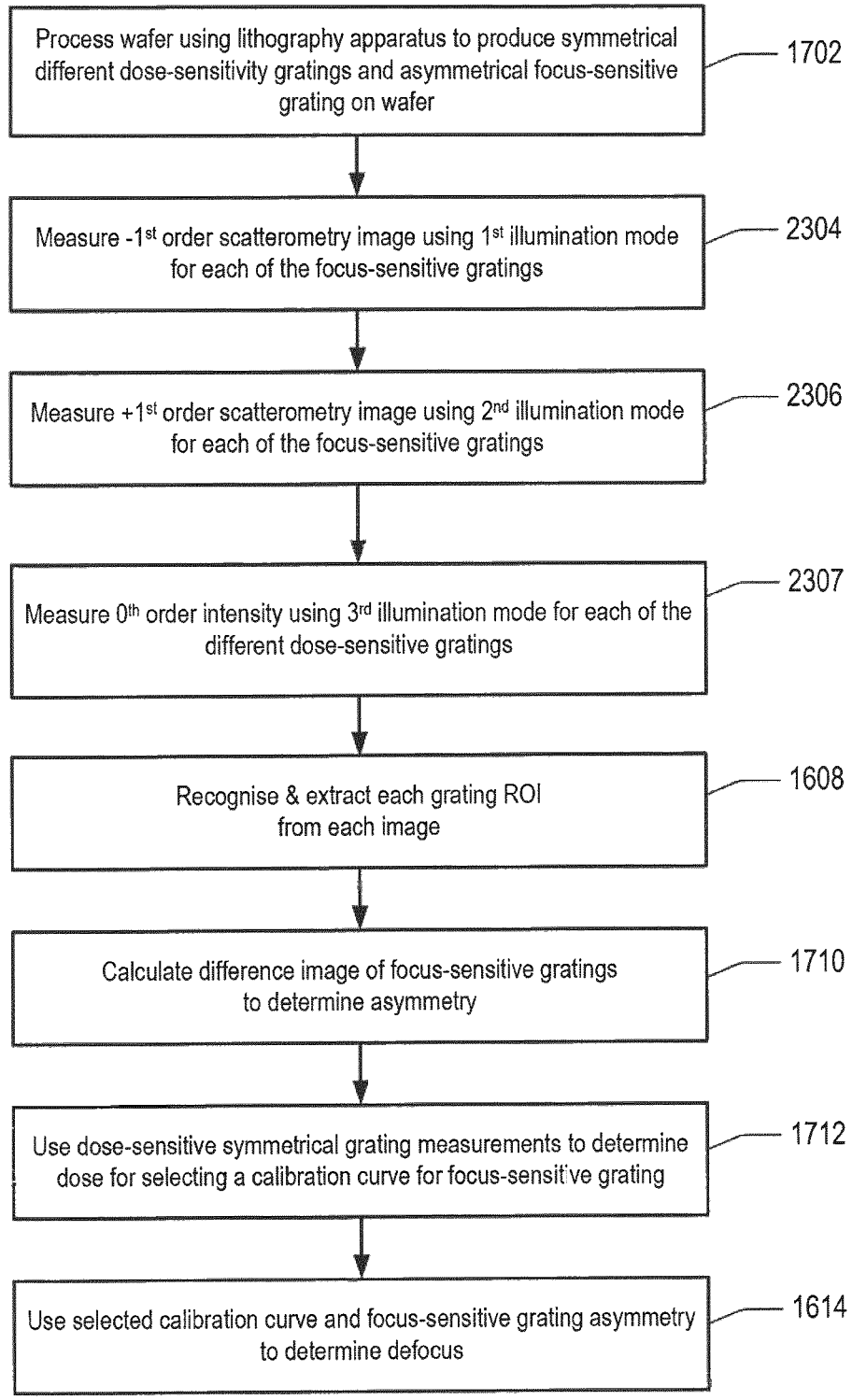

FIG. 23 is a flow chart of a method of determining dose and focus in accordance with another embodiment of the present invention using symmetrical differential dose-sensitive gratings with dark-field and image-plane detection scatterometry.

Figure 24:
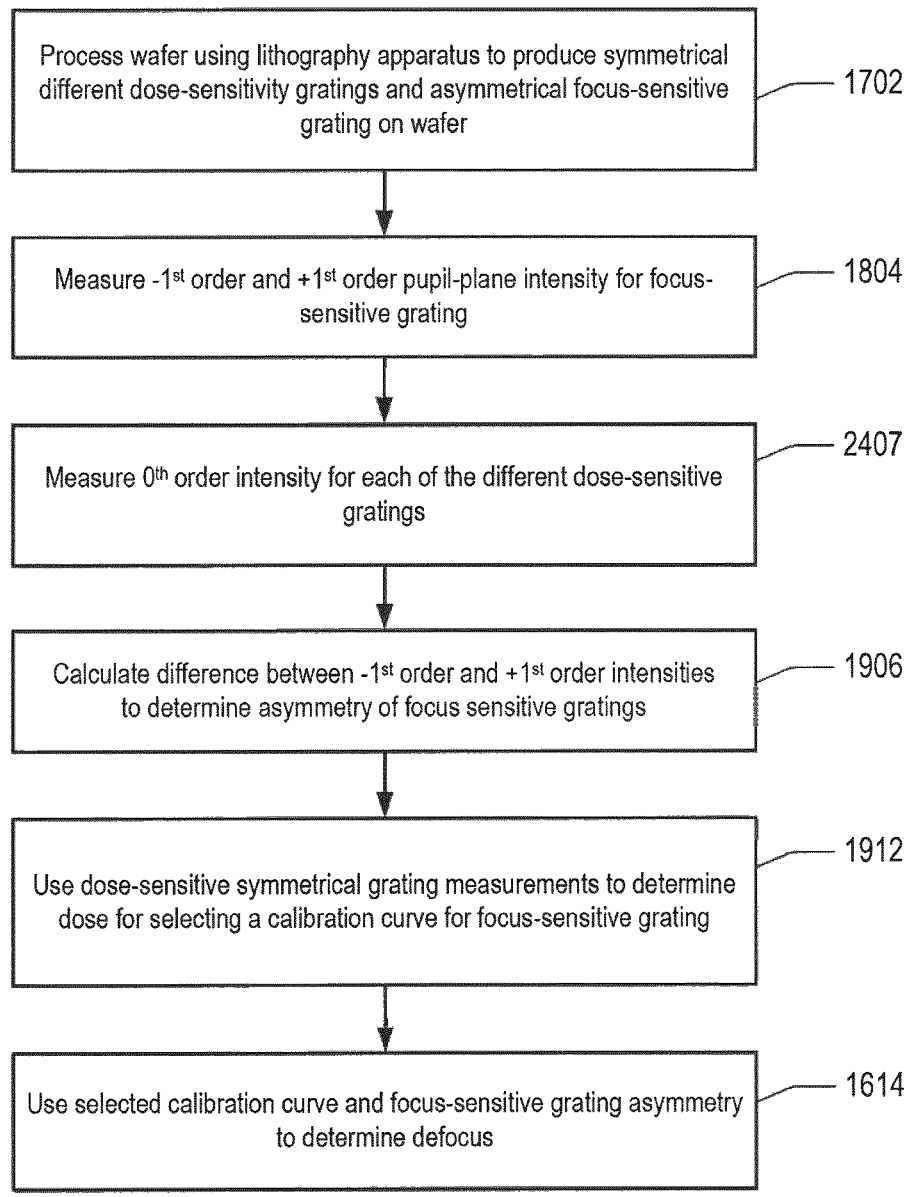

FIG. 24 is a flow chart of a method of determining dose and focus in accordance with another embodiment of the present invention using symmetrical differential dose-sensitive gratings with pupil-plane detection scatterometry.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
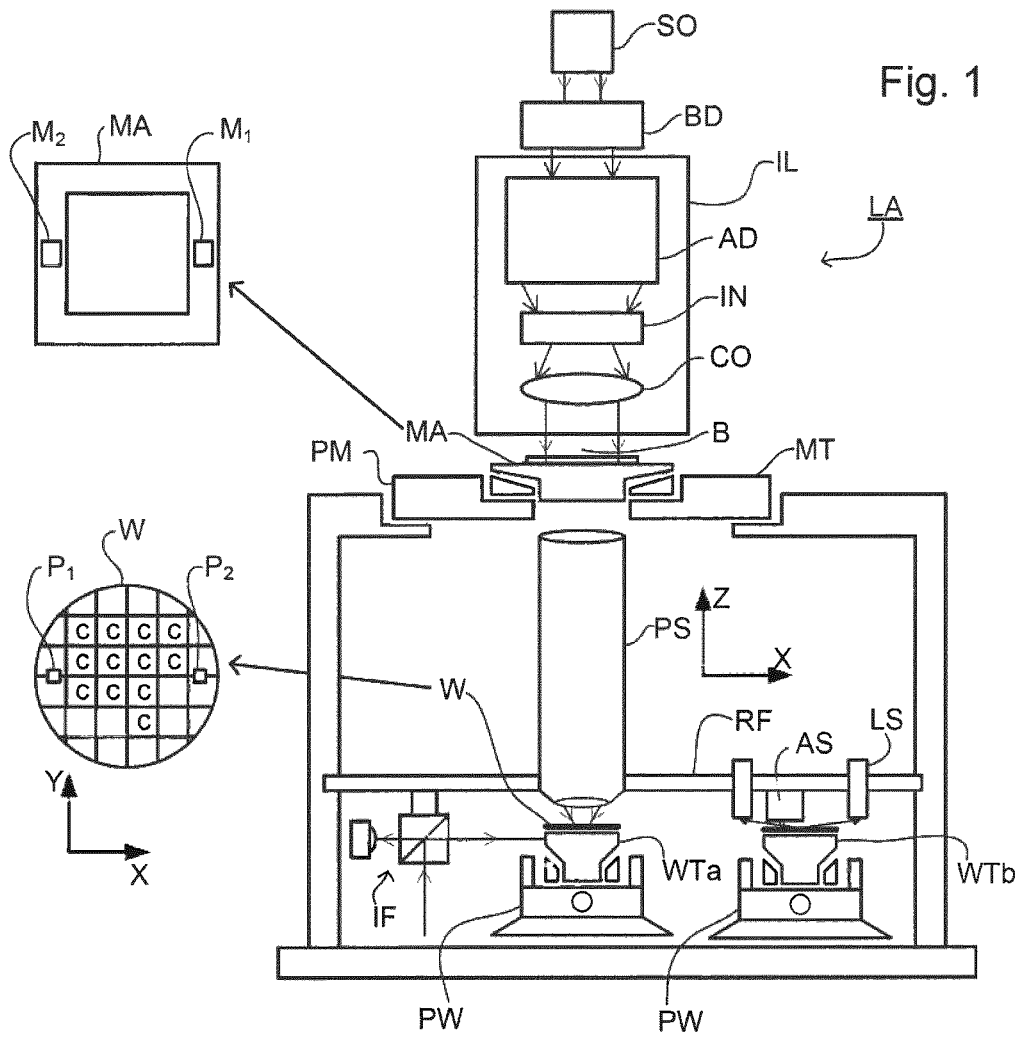
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
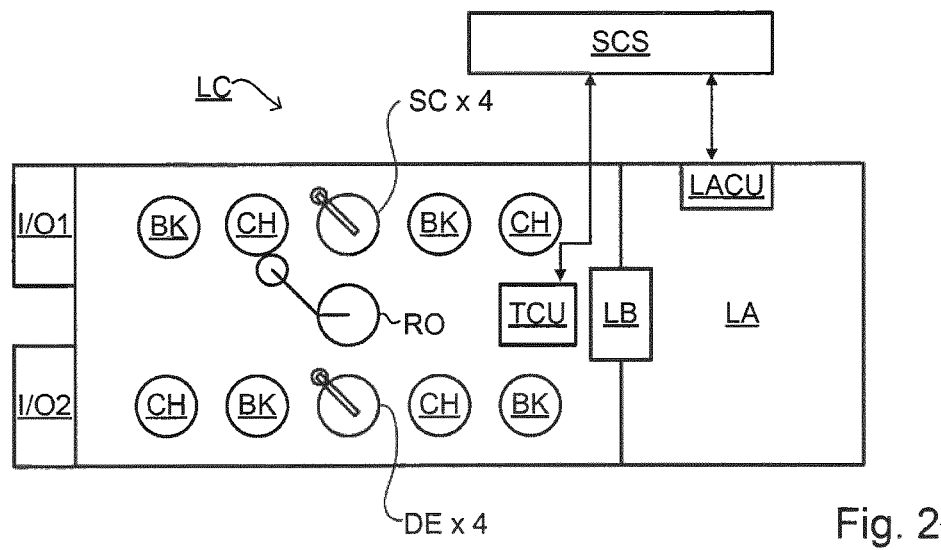
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Examples of dark-field metrology can be found in international patent applications WO 2009/078708 and WO 2009/106279 which documents are hereby incorporated by reference in their entirety. Further developments of the technique have been described in patent publications US20110027704A, US20110043791A and US20120123581A. The contents of all these applications are also incorporated herein by reference. US patent publication number US20110249247A discloses using measured scatterometer signals from focus-sensitive asymmetric target designs to measure defocus of a lithographic apparatus. The contents of that application are incorporated herein by reference. In such a method, asymmetric information, as available in the scatterometer pupil in the form of the difference between −1st and +1st diffraction order intensities, is used to infer scanner defocus from the measured scatterometer signals.

A dark field metrology apparatus suitable for use in embodiments of the invention is shown in FIG. 3(a). A target grating T and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line 0. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target grating T is placed with substrate W normal to the optical axis O of objective lens 16. A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image for an underfilled target may be used as an input for dose and focus metrology, in accordance with embodiments of the present invention.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial sight modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3(c). The aperture plates 13N to 13W can be separately formed and interchanged, or they may be a single aperture plate which can be rotated by 90, 180 or 270 degrees. As mentioned already, the off-axis apertures illustrated in FIG. 3(c) could be provided in field stop 21 instead of in illumination aperture plate 13. In that case, the illumination would be on axis.

FIG. 3(d) shows a third pair of aperture plates that can be used to combine the illumination modes of the first and second pairs. Aperture plate 13NW has apertures at north and east, while aperture plate 13SE has apertures at south and west. Provided that cross-talk between these different diffraction signals is not too great, measurements of both X and Y gratings can be performed without changing the illumination mode.

FIG. 4 depicts a composite target formed on a substrate according to known practice. The composite target comprises four gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to defocus measurement, gratings 32 to 35 are themselves focus-sensitive gratings formed by asymmetric gratings that are patterned in layers of the semi-conductor device formed on substrate W. Gratings 32 to 35 may differ in their orientation, as shown, so as to diffract incoming radiation in X and Y directions. In one example, gratings 32 and 34 are X-direction gratings. Gratings 33 and 35 are Y-direction gratings. Separate images of these gratings can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process, such as focus.

FIG. 6 illustrates how, using for example the method described in application US20110027704A, which is incorporated by reference herein in its entirety, defocus is measured through asymmetry of one or more focus sensitive gratings, as revealed by comparing their intensities in the +1 order and −1 order dark-field images. At step S1, the substrate, for example a semiconductor wafer, is processed through the lithographic cell of FIG. 2 one or more times, to create a structure including the gratings. At S2, using the metrology apparatus of FIG. 3, an image of the gratings is obtained using only one of the first order diffracted beams (say −1). Then, whether by changing the illumination mode, or changing the imaging mode, or by rotating substrate W by 180° in the field of view of the metrology apparatus, a second image of the gratings using the other first order diffracted beam (+1) can be obtained (step S3).

Note that, by including only half of the first order diffracted radiation in each image, the 'images' referred to here are not conventional dark field microscopy images. The individual grating lines will not be resolved. Each grating will be represented simply by an area of a certain intensity level. In step S4, a region of interest (ROI) is carefully identified within the image of each component grating, from which intensity levels will be measured. This is done because, particularly around the edges of the individual grating images, intensity values can be highly dependent on process variables such as resist thickness, composition, line shape, as well as edge effects generally.

Having identified the ROI for each individual grating and measured its intensity, the asymmetry of the grating structure, and hence defocus, can then be determined. This is done by the image processor and controller PU in step S5 comparing the intensity values obtained for +1 and −1 orders for each grating 32-35 to identify any difference in their intensity, and (S6) to determine defocus in the vicinity of the target T.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the physical grating structures of the targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the methods described herein and so calculate exposure dose and also defocus with reduced sensitivity to exposure dose. The program may optionally be arranged to control the optical system, substrate support and the like to perform the steps for measurement of a suitable plurality of target structures.

FIG. 7 illustrates a focus-sensitive asymmetric grating pattern. In FIG. 7, a limited section of only three periods of the grating is shown. In the full grating, the pattern 702 repeats in the vertical and horizontal directions. The pattern 702 may be for example a chrome pattern on a reticle. The parameters w1/w2/w3 may be used to describe aspects of the grating, along with other parameters, such as pitch. When the pattern 702 of FIG. 7 is used in a lithography apparatus to produce a focus-sensitive grating structure on a wafer, the smaller horizontal projections may or may not be resolved, but give a profile with a difference between the right and left side of each printed line (i.e. asymmetry) that is dependent on the focus. A difference in side wall angle is one example of such asymmetry. This sidewall angle dependence on focus of the right side is different than for the left side that has no projections. The pattern 702 therefore leads to a difference in asymmetry, such as printed side wall angle, $\Delta SWA$, between the left and right side of each line, which is dependent on focus of the lithography apparatus during exposure of the grating pattern.

FIG. 8 is a graph that illustrates the dependence of side wall angle difference, $\Delta SWA$, in degrees, on focus setting, F, in nm, of the lithography apparatus using exposure of the grating pattern of FIG. 7. The black curve, labeled 100%, represents a 100% exposure dose. A rough measure of SWA focus sensitivity, FS, is shown and indicates the range of $\Delta SWA$ as focus is varied. Two more curves are shown, for each of 95% and 105% dose. The different doses are shifted down and up respectively from the 100% dose curve. This dose sensitivity, DS, is shown and indicates the range of $\Delta SWA$ as dose is varied. Although the focus and dose sensitivities have different units and so must be compared with caution, for the grating pattern of FIG. 7, the focus sensitivity, FS, over the selected range of focus, −75 to +75 nm, seems much greater than the dose sensitivity, DS, over the selected range of dose, 95% to 105%. However, the dose sensitivity is still enough to cause a problem with accuracy of the focus measurement using asymmetry. This problem is illustrated in FIG. 9.

FIG. 9 is a graph of asymmetry, AS, measured with a scatterometer versus defocus, DF, in nm, of the lithography apparatus using exposure of a grating pattern similar to that of FIG. 7. Five doses are shown, labeled with the doses 20 to 24 mJ/cm$^2$ respectively. Thus FIG. 9 shows the measured asymmetry curves as a function of focus and dose. Using the asymmetric information from the asymmetric focus target suffers from a dose cross-talk effect, indicated with the black arrow. In this example, if dose changes by 1 mJ/cm$^2$ (~5%) from 21 to 22 mJ/cm$^2$ as shown by the arrow, then the cross-talk (focus error) is ~20 nm, as shown by the dashed lines. Embodiments described herein use information of differentially dose-sensitive scatterometer gratings to determine the exposure dose and to decouple the impact of dose cross-talk terms from the actual lithography apparatus defocus value measured using an asymmetric focus-sensitive grating, such as that shown in FIG. 7.

Examples described herein may provide a method to measure the effective scanner dose variation on a wafer and between wafers by means of a target, for example an in-die target, measured using the dark field imaging method.

Examples described herein may include measuring dose based on the reflected intensity of a dose sensitive target by capturing the intensities in the dark field image plane. This limits the pitch range to the allowable range for 1st, or higher, order field detection.

Examples described herein may use a combination of two targets with a different dose sensitivity (contrast or exposure latitude difference) to avoid sensitivity of changes in the process. The two targets can be detected simultaneously (as for example the two bias values in overlay or asymmetry measurements) and separated by image processing (region of interest selection). By simultaneous detection it may be assumed that all error sources that influence the intensity apply in an equal way to both targets. FIGS. 10a and 10b together illustrate an example of differential dose-sensitive symmetric grating patterns.

In FIGS. 10a and 10b, as for FIG. 7, a limited section of only three periods of each grating is shown. In the full grating, the patterns 1002 and 1004 of FIGS. 10a and 10b respectively repeat in the vertical and horizontal directions. The patterns 1002 and 1004 may be for example a chrome pattern on a reticle. The parameter w, along with pitch, defines the grating pattern.

When the patterns of FIG. 10a or 10b are used in a lithography apparatus to produce a dose-sensitive grating structure on a wafer, the structure has a profile with a sidewall angle at both the left and right sides of each printed line that is equally dependent on the focus. For example, the pattern 1002 of FIG. 10a leads to a linewidth, or critical dimension, CD, that is dependent on the focus. However, the CD is more dependent on the dose than for the pattern 702 of FIG. 7. This is illustrated by FIG. 11. The pattern 1004 of FIG. 10b has a different dose sensitivity to that shown in FIG. 11.

FIG. 11 is a graph that illustrates the dependence of critical dimension, CD, on focus setting, F, in nm, of the lithography apparatus using exposure of the grating pattern of FIG. 10a for different doses. The black curve, labeled 100%, represents a 100% exposure dose. A rough measure of CD focus sensitivity, FS, is shown and indicates the range of CD as focus is varied. Two more curves are shown, for each of 95% and 105% dose. The different doses are shifted up and down respectively from the 100% dose curve. This dose sensitivity, DS, is shown and indicates the range of CD as dose is varied. Compared to the printed grating resulting from the pattern 702 of FIG. 7, the printed grating resulting from pattern 1002 of FIG. 10a has a form that is less sensitive to focus of the lithographic apparatus, but is more sensitive to exposure dose of the lithographic apparatus. By changing the linewidth, w, and the pitch, p, the dose sensitivity may be changed. Thus the grating 1002 of FIG. 10a has a different dose sensitivity than the grating 1004 of FIG. 10b.

FIG. 12 illustrates a dose-sensitive asymmetric grating pattern. In FIG. 12, a limited section of only three periods of the grating is shown. In the full grating, the pattern 1202 of FIG. 12 grating repeats in the vertical and horizontal directions. The pattern 1202 may be for example a chrome pattern on a reticle. When the pattern of FIG. 12 is used in a lithography apparatus to produce a dose-sensitive grating structure on a wafer, the smaller horizontal projections are not resolved, but give a profile with a sidewall angle at the right side of each printed line that is dependent on the focus. This sidewall angle dependence on focus of the right side is different than for the left side that has no projections. The pattern 1202 leads to a difference in printed grating side wall angle, ΔSWA, between the left and right side of each line, that is dependent on focus of the lithography apparatus during exposure of the grating pattern, but which is less sensitive to focus than for a grating printed by the pattern 702 of FIG. 7. Being more dose sensitive than the pattern 702 of FIG. 7, and having a dose sensitivity closer to the pattern 1002 of FIG. 10, the pattern 1202 leads to a printed grating with a form that is more sensitive to the exposure dose of the lithographic apparatus compared to the grating resulting from the pattern 702. This is illustrated by FIG. 13.

The parameters w1, w2 and w3 shown in FIG. 12 define aspects of the shape of the asymmetric target. By changing the parameters w1, w2 and w3, different dose sensitivities may be obtained. Thus the dose sensitivity of a parameter measured using the scatterometer, in this example side wall angle, can be adjusted. For the target illustrated in FIG. 7, the parameters w1/w2/w3 are selected to achieve a dose sensitivity much smaller than that of the target illustrated in FIG. 12.

FIG. 13 is a graph that illustrates the dependence of side wall angle difference, ΔSWA, in degrees, on focus setting, F, in nm, of the lithography apparatus using exposure of the grating pattern of FIG. 12 for different doses. The black curve, labeled 100%, represents a 100% exposure dose. A rough measure of SWA focus sensitivity, FS, is shown and indicates the range of ΔSWA as focus is varied. Two more curves are shown, for each of 95% and 105% dose. The different doses are shifted down and up respectively from the 100% dose curve. This dose sensitivity, DS, is shown and indicates the range of ΔSWA as dose is varied. In the same way as discussed with reference to FIGS. 10 and 11, compared to the printed grating resulting from the pattern 702 of FIG. 7, the printed grating resulting from pattern 1202 of FIG. 12 has a form that is more sensitive to exposure dose of the lithographic apparatus. The differential dose sensitivity is weakly dependent on focus, therefore it is advantageous to combine a dark-field asymmetric focus grating in the same target design. This allows correcting the differential dose sensitivity for the scanner actual focus. With a combination of absolute dose target, differential dose target and asymmetric focus target the following parameters can be resolved: Process-insensitive focus, using the asymmetric focus-sensitive target, as described in patent publication US20110027704A. By process-insensitive, it is meant that the dark-field measurement is not sensitive to cross talk variations resulting from processing of layers that make up the substrate and the target. Dose corrected focus, using the examples described herein to determine dose, which is then used to correct focus measurements obtained using the asymmetric focus-sensitive target, as described in patent publication US20110027704A. Process insensitive dose, using the examples described herein to determine dose.

The combination of targets can be exposed in a single Focus-Exposure Matrix (FEM) and the focus and differential dose sensitivities can be obtained from this FEM.

FIG. 14a schematically illustrates a combined focus- and differential dose-sensitive target 1402, suitable for dark-field image-detection scatterometry. Although only three periods of each grating are shown, this is only to represent the type of grating. The patterns are not to scale and in practice will be smaller and repeated in the vertical and horizontal directions. The gratings labeled FSH and FSV are focus-sensitive asymmetric gratings, as described with reference to FIG. 7, with lines in horizontal and vertical directions respectively. Thus FSH and FSV have at least one feature which has a profile that has a form that depends on focus of the lithographic apparatus on the substrate. The gratings labeled DS1 and DS2 are differential dose-sensitive gratings. Thus DS1 has at least one feature which has a form that depends on exposure dose of the lithographic apparatus on the substrate and DS2 has at least one feature which has a form that depends on the exposure dose of the lithographic apparatus on the substrate but which has a different sensitivity to the exposure dose of the lithographic apparatus on the substrate than the first structure.

Creating the differential dose sensitivity is achieved through manipulating the contrast of a typical overlay/focus type grating DS1. In this example, this is done by applying sub resolution segmentation of the regular grating, resulting in grating DS2.

FIG. 14b schematically illustrates a combined focus- and differential dose-sensitive target 1404, suitable for dark-field image-detection scatterometry in relation to the focus-sensitive targets. For the differential dose-sensitive targets rather than being dark-field, it is the specular reflection (zeroth order) that is spatially separated and that has its intensity measured. Thus the target of FIG. 14b is suitable for image-plane detection scatterometry in relation to the differential dose-sensitive targets DS3 and DS4. Again, although only three periods of each grating are shown, this is only to represent the type of grating. The patterns are not to scale and in practice will be smaller and repeated in the vertical and horizontal directions. The gratings labeled FSH and FSV are focus-sensitive asymmetric gratings, as described with reference to FIG. 7, with lines in horizontal and vertical directions respectively. Thus FSH and FSV have at least one feature which has a profile that has a form that depends on focus of the lithographic apparatus on the substrate. The gratings labeled DS3 and DS4 are differential dose-sensitive gratings, with different pitch, but having the same fill factor (linewidth to pitch ratio). Thus DS3 has at least one feature (each line of its grating) which has a form that depends on exposure dose of the lithographic apparatus on the substrate and DS4 has at least one feature (each line of its grating) which has a form that depends on the exposure dose of the lithographic apparatus on the substrate but which has a different sensitivity to the exposure dose of the lithographic apparatus on the substrate than the first structure.

Creating the differential dose sensitivity is achieved through manipulating the pitch and linewidth of the gratings DS3 and DS4. In this example, this is done by changing the pitch of grating DS4 relative to the grating DS3, while keeping the same fill factor as DS3. A specific example is discussed below with reference to FIGS. 20 to 23.

With reference to FIGS. 14a and 14b, a composite target is thus achieved similar to that described with reference to the target of FIG. 4. Thus the four targets in each of FIGS. 14a and 14b (and also for FIG. 15) can all be within a measurement spot formed by an illumination beam of a metrology apparatus. The four targets of FIG. 14a may thus all be simultaneously illuminated and simultaneously imaged in a dark-field scatterometry measurement. The four targets of FIG. 14b may all be simultaneously illuminated and simultaneously imaged in an image-plane detection scatterometry measurement, provided that the separated zeroth order radiation scattered from the dose-sensitive targets DS3 and DS4 can be detected at the same time as the first order ($+1^{st}$ or $-1^{st}$) radiation scattered from the focus-sensitive asymmetric targets FSH and FSV. Such a parallel measurement would require modifications of the apparatus of FIG. 3(a) (such as beam splitters and an additional detector), which as it stands would be able to measure the focus- and dose-sensitive targets in sequence, rather than simultaneously, as described below with reference to FIG. 23.

FIG. 15 schematically illustrates a combined focus- and differential dose-sensitive target 1502, suitable for dark-field image-detection scatterometry. As described for FIGS. 14a and 14b, although only three periods of each grating are shown, this is only to represent the type of grating. The gratings labeled FSH and FSV are again focus-sensitive asymmetric gratings, as described with reference to FIG. 7, with lines in horizontal and vertical directions respectively. The gratings labeled DS3 and DS4 are differential dose-sensitive gratings as described with reference to FIG. 12, with different values of one or more of the parameters w1/w2/w3. Thus DS3 has at least one feature which has a form that depends on exposure dose of the lithographic apparatus on the substrate and DS4 has at least one feature which has a form that depends on the exposure dose of the lithographic apparatus on the substrate but which has a different sensitivity to the exposure dose of the lithographic apparatus on the substrate than the first structure.

FIG. 16 is a flow chart of a method in accordance with an embodiment of the present invention, using asymmetrical differential-dose gratings and an asymmetrical focus sensitive grating with dark-field scatterometry to determine defocus. The method in this example uses asymmetric targets as illustrated in FIG. 15. For FIG. 16, only the horizontal gratings will be mentioned, although the vertical gratings may also be used, in order to separately measure X and Y focus behavior.

In step 1602: Process a wafer using lithography apparatus to produce different dose-sensitivity gratings, DS3 and DS4, and a focus sensitive grating, FSH, on wafer.

In step 1604: Measure −1st order scatterometry image using a 1st illumination mode.

In step 1606: Measure +1st order scatterometry image using a 2nd illumination mode.

In step 1608: Recognise & extract each grating region of interest (ROI) from each image.

In step 1610: Calculate a difference (between −1st and +1st order measurements) image of each grating to determine asymmetry.

In step 1612: Use the asymmetry of the different dose-sensitivity gratings, DS3 and DS4 to calculate a dose value, which is in turn used to select a calibration curve for the focus-sensitive grating, FSH.

In step 1614: Use the selected calibration curve and determined focus-sensitive grating, FSH, asymmetry to determine defocus.

As mentioned above, the method in the example of FIG. 16 used asymmetric targets as illustrated in FIG. 15. However, it will be appreciated that the dose-sensitive targets could be symmetrical, as shown in FIG. 14a as DS1 and DS2 and as shown in FIG. 14b as DS3 and DS4. Such a case is illustrated in FIG. 17, which is a flow chart of a method in accordance with other embodiments of the present invention, using symmetrical differential-dose gratings and an asymmetrical focus sensitive grating with dark-field scatterometry, to determine defocus. Step 1702 is a modified version of step 1602 of FIG. 16, but with symmetrical rather than asymmetrical differential dose gratings. Step 1710 is a modified version of step 1610 of FIG. 16, such that asymmetry is only determined for the focus sensitive targets, FSH and FSV. In step 1712 the measurements of dose-sensitive symmetrical gratings DS1 and DS2 are used to determine dose for selecting a calibration curve for the focus-sensitive grating. The dose value may be obtained from the difference between values of intensity obtained from the regions of interest corresponding to targets DS1 and DS2. The measured intensities are related to dose used in the exposure of the targets. The relationship can be obtained for example by first determining an intensity versus dose calibration curves of intensities for each of the DS1 and DS2 targets as a function of dose via a FEM. Subsequently (for example on a different wafer) measurement of intensity for DS1 and DS2 target structures is performed and a dose value is inferred from the intensities using the intensity versus dose calibration curves.

Alternatively, the relationship can be obtained for example by first determining an intensity difference versus dose calibration curve of the difference in intensities between the DS1 and DS2 targets as a function of dose via a FEM. Subsequently (for example on a different wafer) measurement of a difference of intensity for DS1 and DS2 target structures is performed and a dose value is inferred from the difference in intensity using the intensity difference versus dose calibration curve.

As described with reference to FIGS. 14 and 15, the focus-sensitive and dose-sensitive gratings do not have to be physically apart. They can be one physical target. Detection methods such as described with reference to FIGS. 16 and 17 allow separation of dose-sensitive and focus-sensitive information with one pass of the inspection apparatus. These targets may also be combined on a single location on the wafer, for example by orthogonal placement of both target structure types (dose sensitive target in horizontal direction; focus sensitive targets in vertical direction). This combination is also suitable for pupil-detection scatterometry mode, discussed below with reference to FIG. 18.

Pupil-plane detection scatterometry may also be used, as illustrated by FIG. 18, either alone, as an alternative to, or in combination with dark-field image-detection scatterometry (as described for FIGS. 6, 16 and 17) to obtain the scatterometry signals, for use according to embodiments of the present invention.

FIG. 18 is a flow chart of a method in accordance with an embodiment of the present invention using asymmetrical differential-dose gratings and an asymmetrical focus sensitive grating with pupil-plane detection scatterometry, to determine defocus. The method in this example may use underfilled targets as illustrated in FIGS. 7 and 12. The steps 1602, 1612 and 1614 in FIG. 18 are the same as described with reference to FIG. 16. However steps 1604 to 1610 are replaced with pupil-plane detection steps. In step 1804: Measure the −1st order and +1st order intensity in the pupil-plane, for example using sensor 19 in FIG. 3a. In step 1806: Calculate the difference between −1st order and +1st order intensities to determine asymmetry, for example using processing unit PU in FIG. 3a.

FIG. 19 is a flow chart of a method in accordance with another embodiment of the present invention using symmetrical differential-dose gratings and an asymmetrical focus sensitive grating with pupil-plane detection scatterometry, to determine defocus. As for FIG. 18, the method in this example may use underfilled targets as illustrated in FIGS. 7 and 12. The steps 1702 and 1712 in FIG. 19 are the same as described with reference to FIG. 17. However, compared to FIG. 17, steps 1604 to 1712 are replaced with pupil-plane detection step 1804 described with reference to FIG. 18, step 1906 determining asymmetry for the focus sensitive gratings only and step 1912 using dose-sensitive symmetrical grating measurements.

Step 1912 may be performed using CD reconstruction to determine dose for selecting a calibration curve for the focus-sensitive grating. For the example, CD may be calculated from scatterometry signals, using a full reconstruction cycle. Alternatively a CD measurement of the dose sensitive symmetric or asymmetric target may be made with another metrology method such as CD-SEM (Scanning Electron Microscopy), before deducing dose information from the measured targets. However, as mentioned above, CD-SEM is slow and reconstruction is also time consuming.

The exposure dose can be obtained using dose-sensitive symmetrical target pairs that print differently at the optimal process working point, but that invoke a similar scatterometry signal at the optimal process working point. By proper target design the scatterometry signal difference can be made dependent on the effective exposure dose only.

The operation of this example is based upon the following observations:

(1) For small pitches, p<200 nm, most scatterometers operate sub-resolution. That implies that the instrument cannot directly resolve the pitch of the target.

(2) In particular, the scatterometry signal of dense line/space targets is dominated by the effective medium behavior of the target structure, for example a patterned resist layer.

(3) The patterned layer behaves as a material with a direction-dependent refractive indices $n_x$ and $n_y$. The refractive indices depend largely in the line/space ratio and hardly on the pitch.

The CD of dense line/space targets is dominated by the dose if the workpoint is chosen at the isofocal, i.e. where the CD is least dependent on focus.

As an example, the following target pair may be used:

Target 1, pitch 80 nm, CD 33 nm, fill factor 33 nm/80 nm=0.41; and

Target 2, pitch 100 nm, CD 41 nm, fill factor 41 nm/100 nm=0.41.

FIGS. 10a and 10b (not to scale) show such a target pair suitable for pupil-plane detection scatterometry. Also, in FIG. 14b, DS3 and DS4 schematically represents such a target pair suitable for image-plane detection scatterometry.

For such target pairs, it is observed that, despite the significant difference in pitch, the scatterometry signals are virtually the same. For example, with the pupil intensities I for each target, $$\frac{\Delta I}{I_{rms}} \text{ is less than } 1\%.$$

The scatterometry signal sensitivity to CD variation of each of the target pair is very similar, albeit with a slight scale difference. The same holds for the sensitivity to underlying stack variations. So even though each of the target pair prints differently from the other, the behavior of the scatterometry signal is similar for CD and underlying stack variations. On the other hand, the dose sensitivity is different between the target pair.

FIGS. 20a and 20b illustrate the dose and focus sensitivity of the target pair. FIGS. 20a and 20b show the Bossung plots with focus on the horizontal axis and CD on the vertical axis for the two targets (FIG. 20a: pitch 80 nm, FIG. 20b: pitch 100 nm). Plots are shown for three different exposure doses, BE (Best Exposure), BE+1% and BE-1%. It is apparent that the dose sensitivity is very different, and that the focus sensitivity is quite low for both targets.

FIG. 21 shows the 'effective' CD differences, that is the CD differences weighted with the difference in sensitivity of the scatterometer, of the data shown in FIGS. 20a and 20b. It is apparent that the effective CD difference, as measured using the scatterometer, is very much dependent on the dose, and hardly on the focus.

Further optimization of the target pair design is possible. It is possible to design, or find through simulation or experimentation, other targets with essentially similar scatterometry signal at the same dose, but with a different CD and pitch and therefore a very different dose sensitivity.

Although target pairs are referred to herein, it will be appreciated that three or more targets with different dose sensitivity may be used to calculate the dose, by simply combining the results of measurements of the three or more targets.

FIG. 22 is a flow chart of a method of determining dose in accordance with an embodiment of the present invention using symmetrical differential dose-sensitive gratings. The example method of determining exposure dose of a lithographic apparatus used in a lithographic process on a substrate shown in FIG. 22 is as follows.

In step 2202: Process the wafer using the lithography apparatus to produce a pair of symmetrical different dose-sensitivity gratings, for example as shown in FIGS. 10a and 10b and also for example in FIG. 14b as DS3 and DS4. The lithographic process is used to produce a first structure on the substrate, the first structure having at least one feature which has a form that depends on exposure dose of the lithographic apparatus on the substrate; and the lithographic process is used to produce a second structure on the substrate, the second structure having at least one feature which has a form that depends on the exposure dose of the lithographic apparatus on the substrate but which has a different sensitivity to the exposure dose of the lithographic apparatus on the substrate than the first structure.

In step 2203: Receiving the substrate into the inspection apparatus.

In step 2207: Detecting scattered radiation while illuminating the first structure with radiation to obtain a first scatterometer signal and detecting scattered radiation while illuminating the second structure with radiation to obtain a second scatterometer signal. This step may comprise separating zeroth order scattered radiation from any higher order scattered radiation and detecting the zeroth order scattered radiation to obtain each respective scatterometer signal. This ensures that different amounts of high order diffracted light arising from the different pitches of the target pair is not measured. The illumination radiation may be of a wavelength selected such that the pitch of each of first and second structures is sub-resolution using the selected wavelength. This also ensures that different amounts of high order diffracted light arising from the different pitches of the target pair is not measured.

In step 2212: Using the first and second scatterometer signals to determine an exposure dose value used to produce the first structure, based on: the first structure having at least one feature which has a form that depends on exposure dose of the lithographic apparatus on the substrate; and the second structure having at least one feature which has a form that depends on the exposure dose of the lithographic apparatus on the substrate but which has a different sensitivity to the exposure dose of the lithographic apparatus on the substrate than the first structure. This step may be performed by a processing unit, such as PU in FIG. 3(a) executing computer program instructions. This step may be further based on the forms of the first and second structures having been selected to minimize differences between the first and second scatterometer signals for the same exposure dose. This allows differences in the scatterometer signals to be dominated by the dose sensitivity. The at least one feature of the first structure and the at least one feature of the second structure may comprise gratings with different respective pitches but similar linewidth to pitch ratios. This has the effect of minimizing differences between the first and second scatterometer signals for the same exposure dose by making the direction dependent refractive index the same or similar for each of the target pair.

The method of measuring dose illustrated in FIG. 22 may be applied to methods of measuring focus. This will be illustrated with reference to FIGS. 23 and 24.

Use of a pair of differential dose-sensitive targets such as illustrated in FIG. 14b as DS3 and DS4 is illustrated in FIG. 23, which is a flow chart of a method in accordance with embodiments of the present invention, using symmetrical differential dose-sensitive gratings and an asymmetrical focus sensitive grating with dark-field scatterometry, to determine defocus. The steps are the same as describe for FIG. 17, except steps 2304 and 2306 are modified versions of steps 1604 and 1606, such that the first (or higher) order scatterometry images are only measured for the focus sensitive gratings. Furthermore step 2307 is inserted to measure zeroth order intensity using a third illumination mode for each of the different dose-sensitive symmetrical gratings DS3 and DS4. This step corresponds to step 2207 in FIG. 22. This third illumination mode selects the zeroth order, while blocking any higher orders of scattered radiation from the detector (23 in FIG. 3a). The skilled person will appreciate that this can be achieved for example, by using a suitable aperture 13 and/or field stop 21 (with reference to FIG. 3a). Such arrangements for separating zeroth and higher diffraction orders are described in patent publication US2010201963A1. The contents of that application are incorporated herein by reference.

In accordance with the description of FIG. 22, in step 1712 of FIG. 23, the dose value may be obtained from the difference between values of zeroth order radiation intensity obtained from the regions of interest corresponding to targets DS3 and DS4. The measured intensities are related to dose used in the exposure of the targets. The relationship can be obtained for example by first determining an intensity versus dose calibration curves of intensities for each of the DS3 and DS4 targets as a function of dose via a FEM. Subsequently (for example on a different wafer) measurement of intensity for DS3 and DS4 target structures is performed and a dose value is inferred from the intensities using the intensity versus dose calibration curves.

As described with reference to FIG. 14b, the focus-sensitive and dose-sensitive gratings do not have to be physically apart. They can be one physical target. Detection methods such as described with reference to FIGS. 16, 17 and 23 allow separation of dose-sensitive and focus-sensitive information with one pass of the inspection apparatus. These targets such as shown in FIG. 14b may also be combined on a single location on the wafer, for example by orthogonal placement of both target structure types (dose sensitive target in horizontal direction; focus sensitive targets in vertical direction). This combination is also suitable for pupil-detection scatterometry mode, discussed below with reference to FIG. 24.

Pupil-plane detection scatterometry may also be used, as illustrated by FIG. 24, either alone, as an alternative to, or in combination with dark-field image-detection scatterometry (as described for FIGS. 6, 16, 17 and 23) to obtain the scatterometry signals, for use according to embodiments of the present invention.

FIG. 24 is a flow chart of a method in accordance with another embodiment of the present invention using symmetrical differential dose-senstitive gratings and an asymmetrical focus sensitive grating with pupil-plane detection scatterometry, to determine defocus. As described for FIG. 19, the method in this example may use underfilled targets as illustrated in FIGS. 7 (for the focus-sensitive target) and FIGS. 10a and 10b (for the dose-sensitive target pair). The steps 1702, 1804, 1906, 1912 and 1614 in FIG. 24 are the same as described with reference to FIG. 19 and the previous drawings. However, compared to FIG. 19, step 2307 is inserted to measure zeroth order intensity for each of the different dose-sensitive symmetrical gratings DS3 and DS4. This step corresponds to step 2207 in FIG. 22. The illumination radiation may be of a wavelength selected such that the pitch of each of first and second structures is sub-resolution using the selected wavelength. This ensures that different high order diffraction arising from the different pitches of the pair is not found in the pupil. So, using the methods described with reference to FIGS. 22 and 24 the full pupil signal can be used to determine the CD or dose difference. This increases the precision of the measurement. Furthermore, since detected difference is dominated by one parameter only, i.e. dose, it is not necessary to have a detailed pupil plane image.

Although the 1st diffraction order intensity signal differences are used in examples described above to determine asymmetry, the asymmetry information is present in higher diffraction orders. Any scatterometer signal generation and processing that gives a clear relation between focus or dose and asymmetry will be suitable. Similarly, but in relation to symmetric targets, when the dark field 1st diffraction order intensity signal differences are used in examples described above to determine intensity, the intensity information may be present in higher diffraction orders. Any scatterometer signal generation and processing that gives a clear relation between focus or dose and intensity will be suitable. Embodiments of the present invention are therefore not limited to using 1st order scatterometry signal differences.

Examples described herein improve dose and focus measurement accuracy and reduce constraints on target design (relax requirements on minimizing cost function for dose cross-talk). In practice, these dose sensitive targets may be measured at only a few points on the wafer.

Possible application of examples described herein are in scanner control loops to create as flat a total dose variation as possible thereby compensating for unwanted scanner dose variations, reticle contributions and process contributions.

Examples described herein allow transition of traditional focus dose methodology to in-die compliant target sizes. This is because dark field image detection scatterometry allows separation of diffraction orders scattered from small targets.

Examples described herein allow "orthogonal" detection of dose through differential sensitivity target design, that is, the dose measurement is not sensitive to variations arising from processing of the stack of materials which make up the target. This is because any such variations are common to both of the differently dose-sensitive targets.

Examples described herein allow high sampling density, because small, in-die targets can be used.

Furthermore, when using the object plane image detection, as described with reference to FIGS. 22 and 23, the targets can be made smaller than the spot size of the scatterometer, trading off the measurement precision for target size reduction. Using the methods described with reference to FIGS. 20 to 24, there is no need for full reconstruction and the scatterometer setup recipe creation process is therefore simplified.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of determining an exposure dose of a lithographic apparatus used in a lithographic process on a substrate, the method comprising:
   detecting scattered radiation from first and second structures that are formed on the substrate, the first and second structures having respective first and second exposure dose sensitivities to the exposure dose of the lithographic apparatus, the first and second exposure dose sensitivities being different from each other;
   determining first and second scatterometer signals based on the detecting of the radiation scattered from respective ones of the first and second structures;
   determining first and second intensity differences between non-zeroth order scatterometer signals of respective ones of the first and second scatterometer signals;
   determining first and second asymmetries of the first and second structures based on the first and second intensity differences, respectively; and
   determining the exposure dose value, used to produce the first structure, based on the first and second asymmetries.

2. The method of claim 1, further comprising:
   producing the first and second structures on the substrate using the lithographic process.

3. The method of claim 1, wherein the determining of the exposure dose value comprises minimizing, using the first and second structures, differences between the first and second scatterometer signals for a same exposure dose.

4. The method of claim 1, further comprising producing the first and second structures having gratings with different respective pitches and similar linewidth to pitch ratios.

5. The method of claim 1, wherein the detecting of the scattered radiation comprises:
   separating a zeroth order scattered radiation from a higher order scattered radiation of the detected scattered radiation; and
   detecting the zeroth order scattered radiation.

6. The method claim 1, further comprising:
   illuminating the first and second structures with a radiation while detecting the scattered radiation; and
   selecting a wavelength of the radiation such that a pitch of each of the first and second structures is sub-resolution using the selected wavelength.

7. The method claim 1, wherein the determining of the exposure dose value comprises determining first and second asymmetries of the first and second structures based on the first and second intensity differences, respectively.

8. The method of claim 1, wherein the detecting of the scattered radiation comprises using an image-plane detection scatterometry.

9. The method of claim 1, wherein the detecting of the scattered radiation comprises using a pupil-plane detection scatterometry.

10. The method of claim 1, wherein the detecting of the scattered radiation from the first and second structures is performed simultaneously.

11. The method of claim 1, further comprising:
    using a third structure, on the substrate, having a focus sensitivity to a focus value of the lithographic apparatus;
    detecting scattered radiation from the third structure;
    obtaining a third scatterometer signal from the detected scattered radiation from the third structure; and
    correcting the determined exposure dose value based on the third scatterometer signal.

12. The method of claim 11, further comprising:
    producing the third structure on the substrate using the lithographic process.

13. The method of claim 1, further comprising:
    using a third structure, on the substrate, having a focus sensitivity to a focus value of the lithographic apparatus;
    detecting scattered radiation from the third structure;
    obtaining a third scatterometer signal from the detected scattered radiation from the third structure; and
    determining the focus value, used to produce the third structure, based on the determined exposure dose value and the third scatterometer signal.

14. The method of claim 13, further comprising:
    producing the third structure on the substrate using the lithographic process.

15. The method of claim 13, wherein the determining of the focus value used to produce the third structure comprises selecting a calibration curve based on the determined exposure dose value.

16. The method of claim 13, wherein the determining of the focus value used to produce the third structure comprises using a model with parameters related to the exposure dose value.

17. An inspection apparatus for determining an exposure dose of a lithographic apparatus used in a lithographic process on a substrate, the inspection apparatus comprising:
    an illumination system configured to illuminate first and second structures produced using the lithographic process on the substrate, the first and second structures having first and second features that have first and second exposure dose sensitivities, respectively, to the exposure dose of the lithographic apparatus, the first and second exposure dose sensitivities being different from each other;
    a detection system configured to:
       detect scattered radiation arising from illumination of the first and second structures, and
       obtain first and second scatterometer signals from the detected scattered radiation from the first and second structures, respectively; and
    a processor configured to:
       determine first and second intensity differences between non-zeroth order scatterometer signals of respective ones of the first and second scatterometer signals;
       determine first and second asymmetries of the first and second structures based on the first and second intensity differences, respectively; and
       determine the exposure dose value, used to produce the first structure, based on the first and second asymmetries.

18. The inspection apparatus of claim 17, wherein the first and second structures have forms that minimize differences between the first and second scatterometer signals for a same exposure dose.

19. The inspection apparatus of claim 17, wherein at least one feature of the first structure and at least one feature of the second structure comprise gratings with different respective pitches and similar linewidth to pitch ratios.

20. The inspection apparatus of claim 17, wherein the detection system is further configured to:
  separate a zeroth order scattered radiation from a higher order scattered radiation of the detected scattered radiation; and
  detect the zeroth order scattered radiation.

21. The inspection apparatus of claim 17, wherein the illumination system is configured to illuminate the first and second structures with a radiation having a wavelength such that a pitch of each of the first and second structures is sub-resolution using the wavelength.

22. The inspection apparatus of claim 17, wherein the processor is configured to determine the exposure dose value, used to produce the first structure, based on an asymmetry of at least one feature of at least one of the first and second structures, the asymmetry being dependent on the exposure dose of the lithographic apparatus.

23. The inspection apparatus of claim 17, wherein:
  the illumination system is further configured to illuminate a third structure produced using the lithographic process on the substrate;
  the detection system is further configured to:
    detect scattered radiation arising from illumination of the third structure, and
    obtain a third scatterometer signal from the detected scattered radiation from the third structure; and
  the processor is further configured to correct the determined exposure dose value based on the third scatterometer signal.

24. The inspection apparatus of claim 17, wherein:
  the illumination system is further configured to illuminate a third structure produced using the lithographic process on the substrate, the third structure having a focus sensitivity to a focus value of the lithographic apparatus;
  the detection system is further configured to:
    detect scattered radiation arising from illumination of the third structure, and
    obtain a third scatterometer signal from the detected scattered radiation from the third structure; and
  the processor is further configured to determine the focus value, used to produce the third structure, based on the third scatterometer signal and the determined exposure dose value.

25. The inspection apparatus of claim 24, wherein the processor is configured to:
  select a calibration curve based on the determined exposure dose value; and
  determine the focus value, used to produce the third structure, based on the selected calibration curve.

26. The inspection apparatus of claim 24, wherein the processor is configured to determine the focus value based on the determined exposure dose value and a model with parameters related to the determined exposure dose value.

27. A method of manufacturing devices wherein a device pattern is applied to a series of substrates using a lithographic process, the method comprising determining an exposure dose of a lithographic apparatus using at least one of the substrates, the determining of the exposure dose comprising:
  detecting scattered radiation from first and second structures that are formed on the at least one of the substrates, the first and second structures having respective first and second exposure dose sensitivities to the exposure dose of the lithographic apparatus, the first and second exposure dose sensitivities being different from each other;
  obtaining first and second scatterometer signals from the detected scattered radiation from the first and second structures, respectively;
  determining first and second intensity differences between non-zeroth order scatterometer signals of respective ones of the first and second scatterometer signals, respectively;
  determining first and second asymmetries of the first and second structures based on the first and second intensity differences, respectively;
  determining the exposure dose value, used to produce the first structure, based on the first and second asymmetries;
  and
  controlling the lithographic process for later substrates based on the determined exposure dose value.

* * * * *